US012778890B2

(12) United States Patent
Benvegnu et al.

(10) Patent No.: US 12,778,890 B2
(45) Date of Patent: Nov. 3, 2026

(54) DEVELOPMENT OF A NEW FAMILY OF NANOCARRIERS DERIVED FROM NATURAL TETRAMERIC ACID LIPIDS

(71) Applicants: UNIVERSITE DE RENNES, Rennes (FR); Centre National de la Recherche Scientifique, Paris (FR); École Nationale Supérieure de Chimie de Rennes, Rennes (FR); Institut National des Sciences Appliquées de Rennes, Rennes (FR); Norwegian University of Science and Technology, Trondheim (NO)

(72) Inventors: Thierry Benvegnu, Rennes (FR); Thomas Vives, Servon sur Vilaine (FR); Matthieu Hicguet, Bruz (FR); Sébastien Simon, Trondheim (NO); Johan Sjöblom, Jakobsli (NO)

(73) Assignees: UNIVERSITE DE RENNES, Rennes (FR); Centre National de la Recherche Scientifique, Paris (FR); École Nationale Supérieure de Chimie de Rennes, Rennes (FR); Institut National des Sciences Appliquées de Rennes, Rennes (FR); Norwegian University of Science and Technology Trondheim, Trondheim (NO)

( * ) Notice: Subject to any disclaimer, the term of this patent is extended or adjusted under 35 U.S.C. 154(b) by 126 days.

(21) Appl. No.: 18/709,728

(22) PCT Filed: Nov. 10, 2022

(86) PCT No.: PCT/EP2022/081525
§ 371 (c)(1),
(2) Date: May 13, 2024

(87) PCT Pub. No.: WO2023/083983
PCT Pub. Date: May 19, 2023

(65) Prior Publication Data

US 2025/0009659 A1 Jan. 9, 2025

(30) Foreign Application Priority Data

Nov. 15, 2021 (EP) .................................... 21306582

(51) Int. Cl.

| | |
|---|---|
| ***A61K 9/127*** | (2025.01) |
| ***A61K 9/1271*** | (2025.01) |
| ***C07C 69/608*** | (2006.01) |
| ***C07C 219/10*** | (2006.01) |
| ***C07D 249/04*** | (2006.01) |
| ***C08G 65/00*** | (2006.01) |

(52) U.S. Cl.
CPC .......... *A61K 9/1271* (2013.01); *C07C 69/608* (2013.01); *C07C 219/10* (2013.01); *C07D 249/04* (2013.01); *C08G 65/00* (2013.01); *C07C 2601/08* (2017.05)

(58) Field of Classification Search
CPC .... C07C 55/26; C07C 2601/08; A61K 9/1271
See application file for complete search history.

(56) References Cited

U.S. PATENT DOCUMENTS

2010/0297217 A1* 11/2010 Rowland ................ A61P 35/00
560/116

FOREIGN PATENT DOCUMENTS

| | | | |
|---|---|---|---|
| WO | 2008114015 | A2 | 9/2008 |
| WO | 2023083983 | A1 | 5/2023 |

OTHER PUBLICATIONS

Lutnaes et al (J Org Biomol Chem 2006, vol. 4, pp. 616-620) (Year: 2006).*
Danaei et al (Pharmaceutics, 2018, vol. 10, pp. 1-17) (Year: 2018).*
Foreign Communication from a Related Counterpart Application, International Search Report and Written Opinion dated Feb. 21, 2023, International Application No. PCT/EP2022/081525 filed on Nov. 10, 2022.
Sutton, et al., "Mass spectrometry of polycyclic tetracarboxylic ('ARN') acids and tetramethyl esters : MS of polycyclic tetraprotic acids", Rapid Communications in Mass Spectrometry, vol. 24, No. 21, Nov. 15, 2010, pp. 3195-3204, XP055914701.
Sutton, et al., "Identification of a Novel Ester Obtained during Isolation of C 80 ("ARN") Tetraprotic Acids from an Oilfield Pipeline Deposit", Energy & Fuels, vol. 24, No. 10, Sep. 14, 2010, pp. 5579-5585, XP055914713.

* cited by examiner

*Primary Examiner* — Mark V Stevens
(74) *Attorney, Agent, or Firm* — Conley Rose, P.C.

(57) ABSTRACT

The present invention thus provides a novel family of liposomal compositions (nanocarriers), hereinafter referred to as Tetra-Acidosomes, comprising natural tetrameric acid (TA) lipids and/or novel chemically functionalized tetrameric acid (CFTA) lipids, for drug delivery applications. Use of the disclosed Tetra-Acidosomes as well as methods of synthesis of the Tetra-Acidosomes are also disclosed.

16 Claims, 4 Drawing Sheets

FIG. 1A
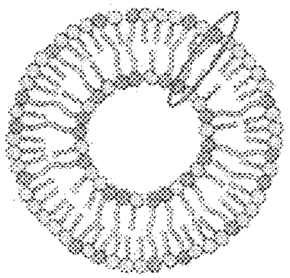
Archaeosome
FIG. 1B
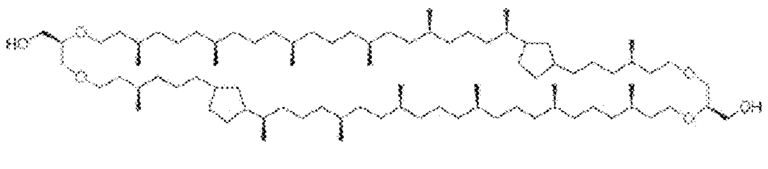
Structure of a tetraether lipid
FIGURE 1
FIG. 2A
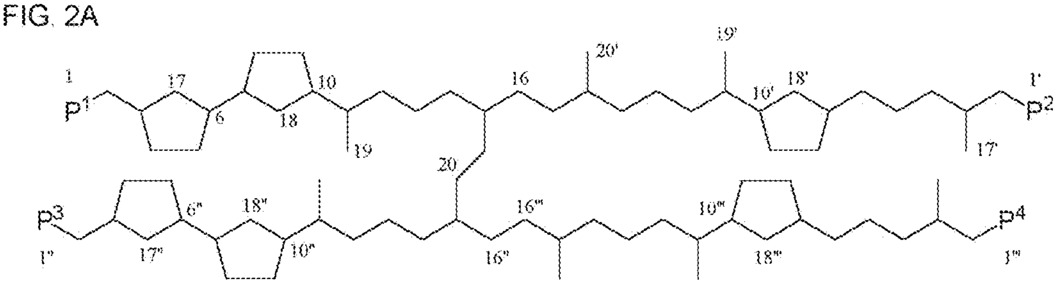
FIG. 2B
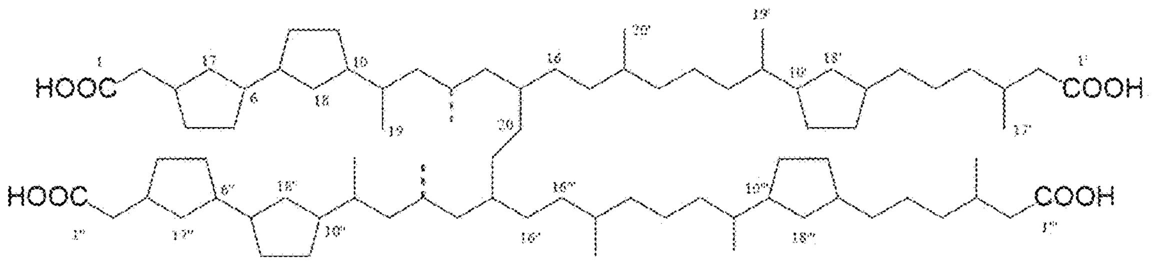
FIGURE 2

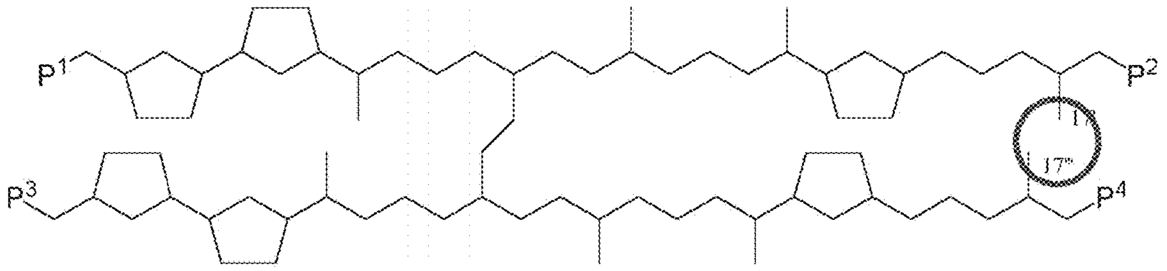
FIGURE 3
FIG. 4A
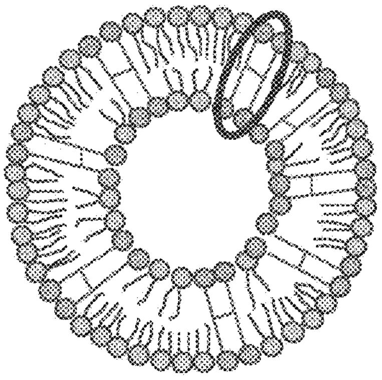
FIG. 4B
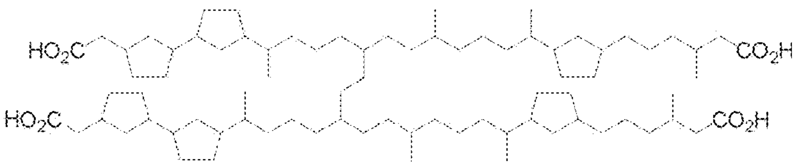
FIGURE 4

DEVELOPMENT OF A NEW FAMILY OF NANOCARRIERS DERIVED FROM NATURAL TETRAMERIC ACID LIPIDS

CROSS-REFERENCE TO RELATED APPLICATIONS

The present application is a filing under 35 U.S.C. 371 as the National Stage of International Application No. PCT/EP2022/081525, filed Nov. 10, 2022, entitled "DEVELOPMENT OF A NEW FAMILY OF NANOCARRIERS DERIVED FROM NATURAL TETRAMERIC ACID LIPIDS," which claims priority to European Application No. 21306582.4 filed with the European Patent Office on Nov. 15, 2021, both of which are incorporated herein by reference in their entirety for all purposes.

DESCRIPTION

Technical Field of the Invention

The present invention thus provides a novel family of liposomal compositions (nanocarriers), hereinafter referred to as Tetra-Acidosomes, comprising natural tetrameric acid (TA) lipids and/or novel chemically functionalized tetrameric acid (CFTA) lipids, for drug delivery applications.

State of the Art

Oral drug delivery is by far the most convenient and advantageous way of drug administration since it is painless and requires no assistance or patient compliance. Other routes, such as intramuscular, intravenous, or pulmonary delivery routes are more difficult to implement, and/or they can hurt or be rejected by the patients.

Currently, more than 60% of the conventional, small molecules (e.g. <800 Da) drug products available in the market are taken orally. However, this is very challenging in the case of therapeutic peptides/proteins and nucleic acids owing to their degradation in the gastro-intestinal (GI) environment (stomach and intestine) and their low permeability to pass through the intestinal barrier into the blood. Indeed, this is a class of drug compounds with significant molecular size, and unique therapeutic properties that are not efficiently taken up in the body which means a poor bioavailability when managed orally. Only a few scattered examples of routine oral applications or clinical trials of peptide drug exist (e.g. Desmopressin, Cyclosporin A).

The gastrointestinal (GI) environment (i.e. stomach and intestine) is surrounded by a protective barrier to enclose GI fluids needed for digestion. The main components of this barrier are a mucus layer (a gel-like coating) and a lining of epithelial cells. The wanted scenario during oral drug delivery is that the therapeutic components are transported from the inside of the gastrointestinal tract, through the mucus and epithelial barrier, and into the blood circulation system. The low delivery efficiency or orally managed peptides/proteins and nucleic acids is mainly due to 1) their degradation by the acidic pH and proteolytic enzymes in the GI environment, and 2) their low mucosal permeability.

This situation can be improved by using liposome nanocarriers, encapsulating peptides/proteins and nucleic acids. Nanoencapsulation of peptides has gained considerable attention as a way of protecting the peptides against the harsh GI environment and providing better adhesion and interactions with the mucus. Mucus-inert nanocarriers favour the penetration of the nanocarriers into the mucus and increase the time available for the drug to be released from the carrier and transported into the blood. The detailed delivery mechanism is, however, still debated.

Polymeric nanoparticles, nanoemulsions, and liposomes have all been investigated as nanocarriers to improve the bioavailability of peptides/proteins and nucleic acids. So far, they are not efficient enough to overcome the GI barriers. However, the performances of the best current systems are still insufficient for medical applications and their price is too high. One example is insulin, where the most promising studies only show 10 to 20% oral bioavailability of insulin in animals [1]. Such low bioavailability will result in high manufacturing costs to deliver standard doses of the drug. Hence, it remains a big scientific and technological challenge to treat diabetic patients orally.

Liposomes are spherical colloids/vesicles consisting of an aqueous interior enclosed by at least one lipid bilayer. A novel class of liposomal nanocarriers, named Archaeosomes, were recently introduced as robust vehicles for oral peptide delivery [2, 3](FIG. 1A). The Archaeosomes were composed of a monolayer of Archaeal tetraether lipids (natural or synthetic) together with conventional bilayer-forming lipids, and therapeutic peptides in the aqueous interior. The Archaeal lipids consist of a macrocyclic core, containing up to four cyclopentane rings per chain, and a polar head group at each terminal end (FIG. 1B). Compared to conventional liposomes, Archaeosomes have shown long-term stability in the presence of stress factors such as low pH, bile slats or lipases [4]. Furthermore, in vivo studies have shown improved oral bioavailability of several peptides such as insulin [5], vancomysin, and hepatitis B drug Myrcludex B [6]. Despite their remarkable stability toward chemical and enzymatic degradation, there are two main obstacles currently limiting their uses as nanocarriers in oral drug delivery:

- the oral bioavailability of Archaeosomes is higher than for conventional liposome formulations, but it is not high enough for medical applications. Novel Archaeal lipid structures can both enhance GI protection and mucus penetration as they are easily graftable with muco-inert polymers like polyethylene glycol [7].
- costs and availability of the Archaeal lipids can limit the commercial potential.

Currently, they are extracted and purified from cultured archaeal biomass [8] or by synthesis from simpler components [9], which costs exceeding $5,000 per gram. New sources of Archaeal lipids could make them more affordable.

Thus there is still a need to generate new nanocarriers available to overcome the GI barriers, that do not have the side effects described above.

DESCRIPTION OF THE INVENTION

Natural TA lipids (also called ARN Acid [10]), extracted from calcium naphthenate deposits [11], have a "H-shaped" structure, four carboxylic acids with four to eight cyclopentane rings in the hydrocarbon skeleton and a molar mass in the range of 1227-1235 $g \cdot mol^{-1}$. The molecule is considered as composed of two moieties with one on the left part of the molecule and the other on the right part, which means that the polar heads $P^1$ and $P^3$ are positioned on the left ends of the lipids while the polar heads $P^2$ and $P^4$ are on the right ends of the lipids (FIG. 2A). The most abundant TA lipid has six cyclopentane rings (formula (Ic)), a molar mass of 1232.01 $g \cdot mol^{-1}$ with a raw formula $C_{80}H_{142}O_8$ and the structure was the first identified by Lutnaes et al. in 2006 [12]. It was also established that $C_{81}$ (X=$CH_3$, Y=H) analogs which lose the symmetry because of an additional $CH_3$ and $C_{82}$ (X=Y=$CH_3$) analogs, are present in the deposits in minor proportions [13] (FIG. 2B). The $C_{81}$ analogs lose the symmetry because of an additional $CH_3$. Additional TA lipids differing by their number of cyclopentane (4, 5, 7 or 8) (formula (Ia), (Ib), (Id) and (Ie)) are also present but in a low proportion (<10% in weight). Natural TA lipids have the following general formula (Ia), (Ib), (Ic), (Id), or (Ie):

(Ia)

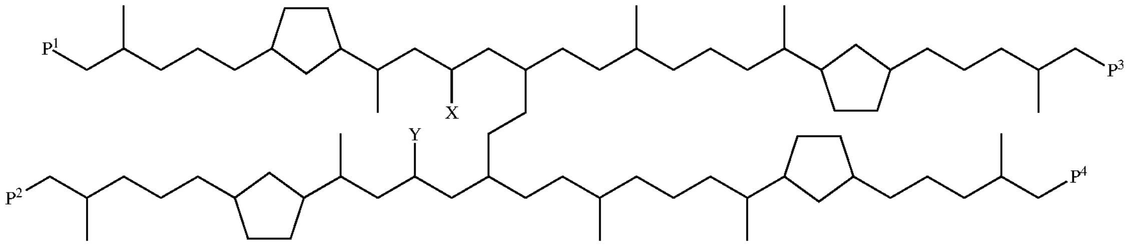

(Ib)

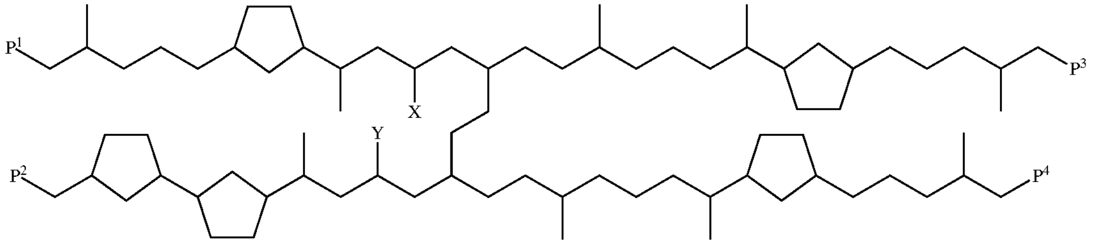

(Ic)

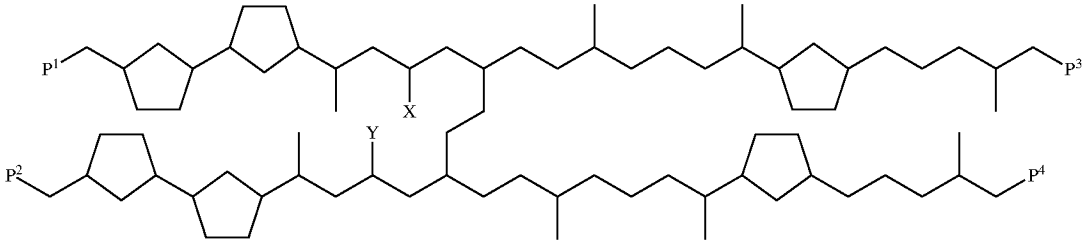

(Id)

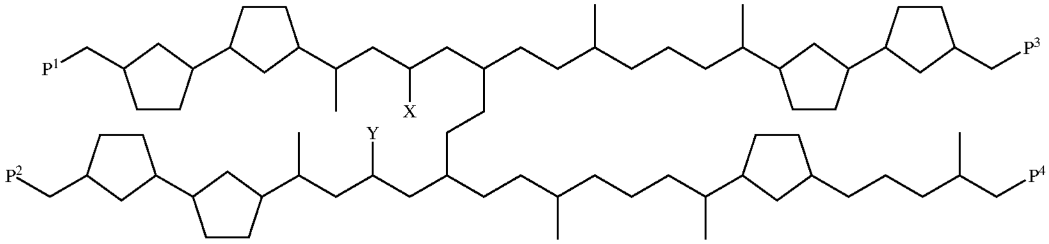

(Ie)

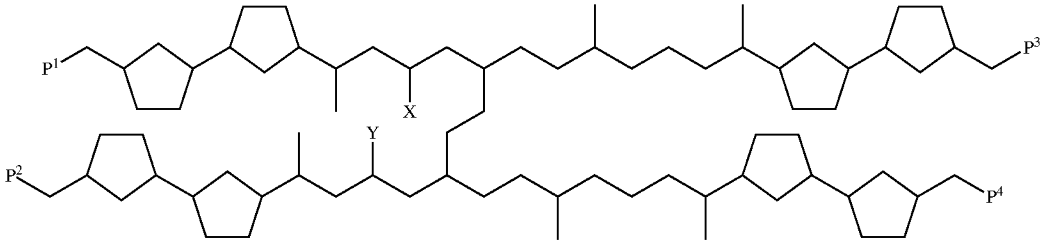

wherein $$P^1 = P^2 = P^3 = P^4 = \text{COOH};$$

X and Y are independently H or $CH_3$.

The present invention provides novel lipid compounds which are chemically functionalized TA (CFTA) lipids comprising four terminal COOH which allow the introduction of many functions (polyethylene glycol (PEG), fluorescent probes, targeting ligands, cationic moieties). The origin of these complex molecules (oil industry waste product) with huge potential pharmaceutical applications, ensures low prices, facilitating future commercialization. The new chemically functionalized tetrameric acids were produced through highly efficient chemical processes. PEGylation of tetrameric acids was achieved using peptide coupling reactions to give the corresponding PEGylated tetrameric acids. More specifically, a method based on selective esterification reactions, was developed to differentiate the four carboxylic acids of the lipids and control the number of PEG chains introduced on the lipids but also on which part of the molecule the chains are added (especially, asymmetrical functionalization of the two carboxylic acid groups at one side of the lipid). Fluorescent probes were grafted to the lipids to allow the monitoring of the liposomes with analytical methods of fluorescence. Cationic tetra-acids were synthesized through esterification reactions with choline chloride for nucleic acids delivery. These formulations were found to exhibit stability with time and they are suitable for encapsulation of both hydrophilic and hydrophobic substrates (including probes).

An object of the present invention is therefore a novel lipid compound having the following general formula (II):

(II)

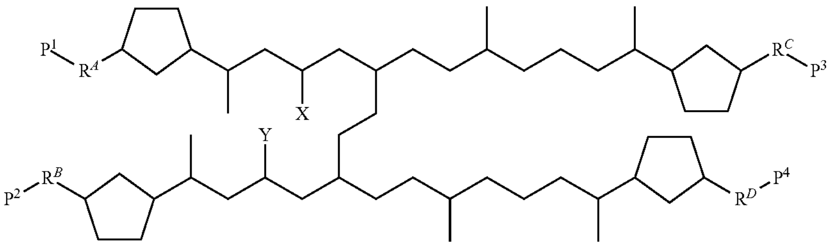

wherein $R^A$, $R^B$, $R^C$ and $R^D$ independently represent a linear or branched, aliphatic or alicyclic, saturated, hydrocarbon group comprising from 2 to 8 carbon atoms, preferably $R^A$, $R^B$, $R^C$ and $R^D$ independently represent

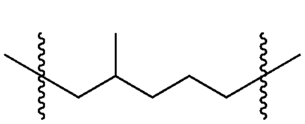

or

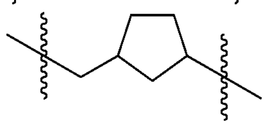

, in which  is the point of attachment to either $P^1$, $P^2$, $P^3$, and $P^4$ or the main molecule;

$P^1$, $P^2$, $P^3$, and $P^4$ are the same or different, and each represents one of the following substituents:

- $CH_2OH$;
- COOH;
- $COOR^1$, with $R^1$ which represents an aliphatic linear or branched, saturated or unsaturated alkyl chain with a number of carbon atoms between 1 to 22, especially 4 carbon atoms (butyl chain);
- $A^1$-$CH_2$—$CH_2$—$N^+(CH_3)_3$, $X_2^-$, $X_2$ representing a halogen or a sulfonate, $A^1$ representing an ester (OC(O)) bond;
- $A^2$-$(PEG_{X1}$-$A^3)_n$-$R^2$, n being equal to 0 or 1, $PEGx_1$, being a polyethylene glycol of molecular weight $X_1$, $X_1$ being less than or equal to 5000 daltons, $A^2$ and $A^3$ possibly being identical or different and representing an ester (C(O)O), an amide (C(O)NH), a triazole, $R^2$ representing a methoxy group, a targeting agent (peptide, antibody, vitamin) or a probe (Nile Red, fluorescein, . . . );

X and Y are independently H or $CH_3$.

In these novel lipid compounds of general formula (II) above described, it is provided that $P^1$, $P^2$, $P^3$, and $P^4$ are not all simultaneously COOH.

According to a particular embodiment of the present invention, in the novel lipid compounds of general formula (II) above described, it is provided that $P_1$, $P_2$, $P_3$, and $P_4$ are the same or different, and each represents one of the following substituents

- $A^1$-$CH_2$—$CH_2$—$N^+(CH_3)_3$, $X_2^-$, $X_2$ representing a halogen or a sulfonate, $A^1$ representing an ester (OC(O)) bond;
- $A^2$-$(PEG_{X1}$-$A^3)_n$-$R^2$, n being equal to 0 or 1, $PEGx_1$, being a polyethylene glycol of molecular weight X1, X1 being less than or equal to 5000 daltons, $A^2$ and $A^3$ possibly being identical or different and representing an ester (C(O)O), an amide (C(O)NH), a triazole, $R^2$ representing a methoxy group, a targeting agent or a probe. For example, the targeting agent is chosen from the group consisting of a peptide, an antibody, a vitamin; the probe is preferably a fluorescent probe chosen from the group consisting of Nile Red, fluorescein.

According to another particular embodiment of the present invention, in the novel lipid compounds of general formula (II) above described, it is provided that $P^1$, $P^2$, $P^3$, and $P^4$ are the same or different, and each represents one of the following substituents:

- $A^1$-$CH_2$—$CH_2$—$N^+(CH_3)_3$, $X_2^-$, $X_2$ representing a halogen or a sulfonate, $A^1$ representing an ester (OC(O)) bond;
- $A^2$-$(PEG_{X1}$-$A^3)_n$-$R^2$, n being equal to 0 or 1, $PEGx_1$, being a polyethylene glycol of molecular weight X1, X1 being less than or equal to 5000 daltons, $A^2$ and $A^3$ possibly being identical or different and representing an ester (C(O)O), an amide (C(O)NH), a triazole, $R^2$ representing a methoxy group.

According to a particular embodiment of the present invention, the novel lipid compounds have the following general formula (IIa), (IIb), (IIc), (IId), or (IIe)

(IIa)

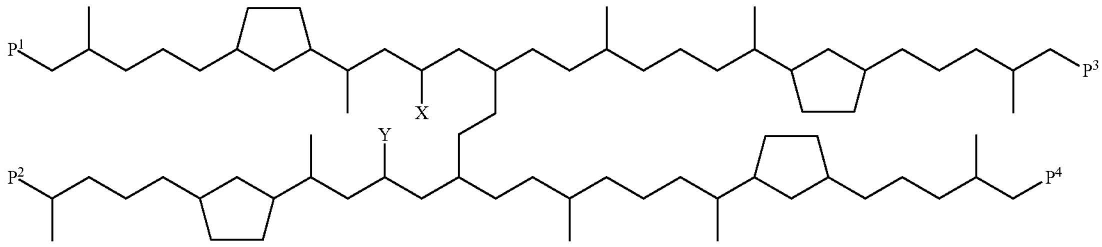

-continued (IIb)

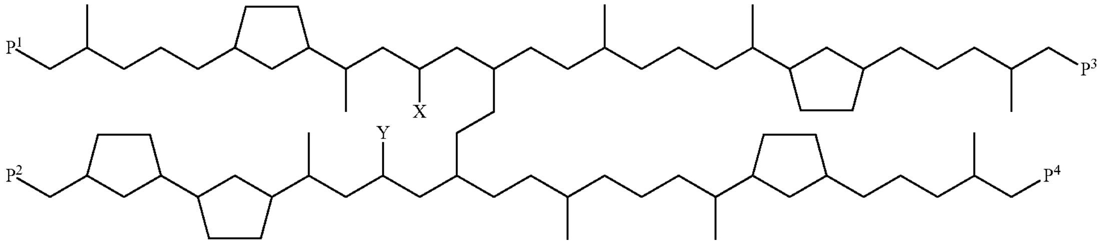

(IIc)

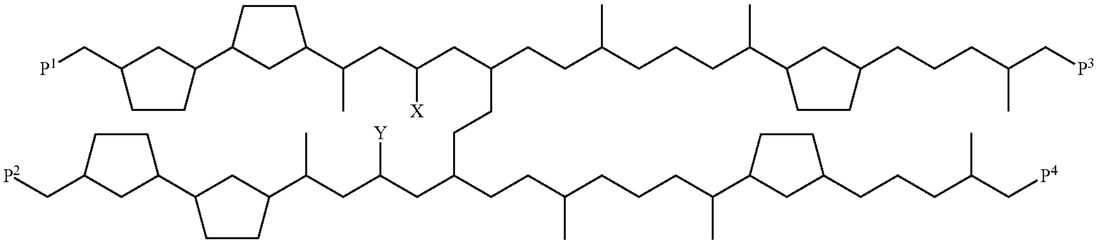

(IId)

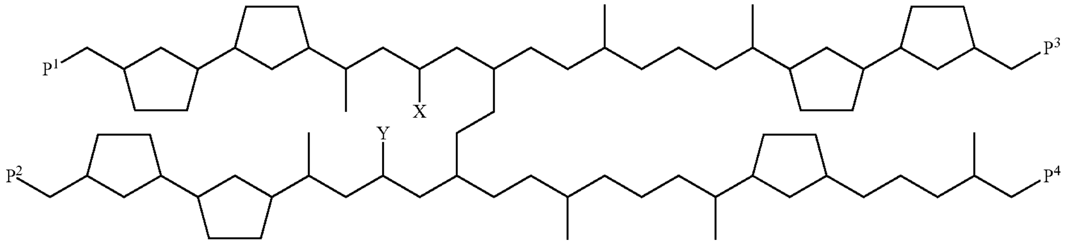

(IIe)

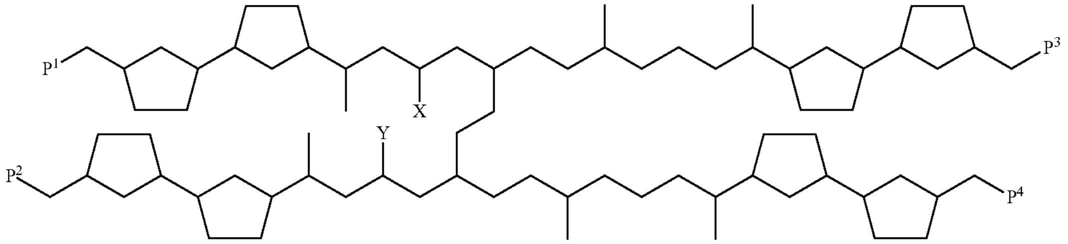

wherein

X, Y, $P^1$, $P^2$, $P^3$, and $P^4$ are as above described.

The present invention also provides a novel family of stable liposomal compositions (nanocarriers) with low polydispersity indexes (e.g. less than 0.3, preferably less than 0.1) and diameters ranging from about 30-40 nm to less than about 250 nm, preferably of less than 200 nm, and are hereinafter referred to as Tetra-Acidosomes. They are liposomes which are prepared for instance by advanced microfluidic techniques with one or more tetrameric acid (TA) lipids extracted from oil industry waste products (calcium naphthenate deposits) and/or one or more natural molecules chemically functionalized (novel CFTA lipids), possibly in combination with traditional phospholipids (e.g. EggPC) and/or cholesterol, for drug delivery applications; thus providing fine tuning of the protection and transport properties of the Tetra-acidosomes as well as cell active targeting and biopharmaceutical characterizations. These innovative liposomal compositions (nanocarriers) designed mainly for oral peptide/protein and nucleic acid drug delivery, allow to efficiently deliver therapeutic drugs into the body due to their resistance to gastrointestinal environment (GI) induced by the tetrameric acid structure and the unique possibilities to control their interactions with the mucus and epithelial barrier through tetrameric acid functionalization. Indeed their H-shaped structure stiffens the vesicle by limiting the flip-flop movements. The presence of four negatively charged carboxylate groups allows to increase permeability of the intestinal wall. Finally, the presence of the 4 terminal COOH allows the introduction of many functions (Polyethylene Glycol (PEG), fluorescent probes, targeting ligands) required to stabilize these nanocarriers, and/or to improve oral bioavailability and mucus/intestinal permeability, and/or to conduct biopharmaceutical studies.

Another object of the present invention is therefore a tetra-acidosome comprising a lipid compound of the present invention as above defined, i.e. a lipid compound having the following general formula (II)

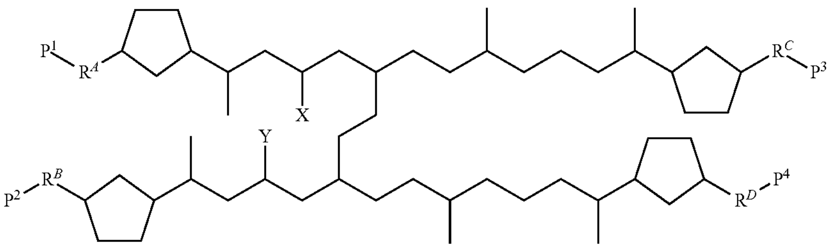

(II)

wherein $R^A$, $R^B$, $R^C$ and $R^D$ independently represent a linear or branched, aliphatic or alicyclic, saturated, hydrocarbon group comprising from 2 to 8 carbon atoms, preferably $R^A$, $R^B$, $R^C$ and $R^D$ independently represent

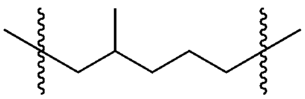

or

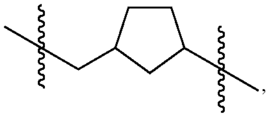

, in which  is the point of attachment to either $P^1$, $P^2$, $P^3$, and $P^4$ or the main molecule;

$P^1$, $P^2$, $P^3$, and $P^4$ are the same or different, and each represents one of the following substituents:

- $CH_2OH$;
- COOH;
- $COOR^1$, with $R^1$ which represents an aliphatic linear or branched, saturated or unsaturated alkyl chain with a number of carbon atoms between 1 to 22, especially 4 carbon atoms (butyl chain);
- $A_1$-$CH_2$—$CH_2$—$N^+(CH_3)_3$, $X_2^-$, $X_2$ representing a halogen or a sulfonate, $A^1$ representing an ester (OC(O)) bond;
- $A^2$-($PEG_{X1}$-$A^3$)$_n$-$R^2$, n being equal to 0 or 1, $PEGx_1$, being a polyethylene glycol of molecular weight X1, X1 being less than or equal to 5000 daltons, $A^2$ and $A^3$ possibly being identical or different and representing an ester (C(O)O), an amide (C(O)NH), a triazole, $R^2$ representing a methoxy group, a targeting agent (peptide, antibody, vitamin) or a probe (Nile Red, fluorescein, . . . );

X and Y are independently H or $CH_3$.

According to a particular embodiment of the present invention, the tetra-acidosome of the present invention comprises a lipid compound having the following general formula (II) and wherein it is provided that $P_1$, $P_2$, $P_3$, and $P_4$ are the same or different, and each represents one of the following substituents:

- $A^1$-$CH_2$—$CH_2$—$N^+(CH_3)_3$, $X_2^-$, $X_2$ representing a halogen or a sulfonate, $A^1$ representing an ester (OC(O)) bond;
- $A^2$-($PEG_{X1}$-$A^3$)$_n$-$R^2$, n being equal to 0 or 1, $PEGx_1$, being a polyethylene glycol of molecular weight X1, X1 being less than or equal to 5000 daltons, $A^2$ and $A^3$ possibly being identical or different and representing an ester (C(O)O), an amide (C(O)NH), a triazole, $R^2$ representing a methoxy group, a targeting agent or a probe. For example, the targeting agent is chosen from the group consisting of a peptide, an antibody, a vitamin; the probe is preferably a fluorescent probe chosen from the group consisting of Nile Red, fluorescein.

According to another particular embodiment of the present invention, the tetra-acidosome of the present invention comprises a lipid compound having the following general formula (II) and wherein it is provided that $P^1$, $P^2$, $P^3$, and $P^4$ are the same or different, and each represents one of the following substituents:

- $A^1$-$CH_2$—$CH_2$—$N^+(CH_3)_3$, $X_2^-$, $X_2$ representing a halogen or a sulfonate, $A^1$ representing an ester (OC(O)) bond;
- $A^2$-($PEG_{X1}$-$A^3$)$_n$-$R^2$, n being equal to 0 or 1, $PEGx_1$, being a polyethylene glycol of molecular weight X1, X1 being less than or equal to 5000 daltons, $A^2$ and $A^3$ possibly being identical or different and representing an ester (C(O)O), an amide (C(O)NH), a triazole, $R^2$ representing a methoxy group.

According to the present invention, the term “Tetra-acidosome” means a liposomal carrier consisting of an archaeosome comprising a lipid compound of the present invention and/or a natural tetrameric (TA) lipid. In other words, a tetra-acidosome derives from an archaeosome wherein all or part of the tetraether lipids are replaced by lipid compounds of the present invention and/or natural tetrameric acid (TA) lipids.

According to a particular embodiment of the present invention, a tetra-acidosome as described above has an average size <250 nm, preferably a, average size <200 nm, and/or a polydispersity index (PDI)<0.3.

According to a particular embodiment of the present invention, a tetra-acidosome as described above further comprises an encapsulated molecule of interest.

The use of TA and/or CFTA lipids in nanocarriers for peptides/proteins and nucleic acids delivery has never been studied before. The unique structure of the molecules allows multiple opportunities to chemical functionalization, providing CFTA lipids, which allows fine tuning of the protection and transport properties of the Tetra-Acidosomes. This new approach overcomes the limitations met with Archaeosomes in several ways:

- The characteristics “H” structure, not found in conventional Archaeal lipids, make the lipid bilayer in the Tetra-Acidosomes more rigid by reducing transbilayer flip-flop motions. This will provide better protection of the therapeutic peptides against the harsh GI environment [14].

The presence of four carboxylic acid groups, lacking in conventional Archaeal lipids, enable incorporation of a large variety of functionalities by synthetic routes based on peptidic coupling reactions and Huisgen "click" cycloadditions. In this way, the presence of 1 to 4 dyes (e.g. Nile Red or fluorescein) introduced at one or two terminal ends of the TA lipids, provides original biological lipid probes designed for biopharmaceutical characterizations of Tetra-Acidosomes. In particular, TA lipids possessing one or two similar dyes (e.g. Nile Red or fluorescein) at each side of the lipid backbone will furnish fluorescent tri- and tetra-Nile Red TA and tri- and tetra-fluorescein TA that will constitute an efficient donor (fluorescein-based TA) and acceptor (Nile Red-based TA) dye pair for Fluorescence Resonance Energy Transfer (FRET) studies [15]. Besides, the controlled introduction of one or two identical dyes (e.g. Nile Red of fluorescein) at one side of the TA lipid will furnish fluorescent mono- and di-labeled TA lipids designed for Fluorescence Recovery After Photobleaching (FRAP) experiments. This opens for studying the nanoparticle stability in the gastrointestinal tract and intestinal permeability by FRET and interactions between the nanocarriers and the mucus by FRAP. The presence of four identical probes is also suitable for biopharmaceutical studies.

Furthermore, asymmetrical incorporation of polyethylene glycol (PEG) on the TA structure results in PEGylated TA lipids (two PEG chains at one side of the lipid) that can give PEG-coated nanoparticles to improve oral bioavailability and mucus/intestinal permeability [16]. The PEG chains can be functionalized by a targeting ligand (peptides, antibodies, vitamins, etc. . . . ) at their terminal ends in order to exhibit active targeting through cell recognition and uptake by cellular membrane receptors.

Additionally, the four carboxylic acids can be reduced into hydroxyl functions to provide a tetraol lipid as a more hydroxylated analog of tetraether diols found in Archaeosomes.

Finally, the introduction of cationic moieties based on choline units onto TA lipids through esterification reactions led to cationic versions of Tetra-Acidosomes valuable for nucleic acids delivery.

The presence of carboxylic groups on TA will also negatively charge the Tetra-Acidosomes at neutral pH. This charge could enhance the permeability of the intestinal wall, which would favor the drug delivery, as it has recently been shown on negatively charged silica nanoparticles [17].

Calcium naphthenate deposits will be used as the source of TA lipids. These typically contain 20 to 40 wt % of the molecules, which can be easily extracted to obtain 80-90% purity [18]. This abundancy will significantly reduce the time of lipid preparation compared to traditional lipid sources.

Another object of the present invention is therefore the use of a tetra-acidosome as described above, as a carrier, in particular as a carrier to the gastrointestinal environment (GI).

Another object of the present invention is a tetra-acidosome as described above, for use as a drug.

Another object of the present invention is a synthetic method of a novel lipid compound as described above comprising a step of reacting TA lipids with a reducing agent, an alcohol, an amine or an ester.

BRIEF DESCRIPTION OF THE FIGURES

FIG. 1 represents (FIG. 1A) an Archaeosome (encircled tetraether lipid) (FIG. 1B) the detailed structure of a tetraether lipid present in *Sulfolobus acidocaldarius.*

FIG. 2 represents (FIG. 2A) a simplified representation of the most abundant TA lipids with P standing for polar head (for TA lipids $P^1$=$P^2$=$P^3$=$P^4$=COOH) (FIG. 2B) a suggested structure of $C_{81}$ or $C_{82}$ TA lipids. The two dotted lines represent the two methyl groups that can be present to explain one or two carbons in addition to the 80 initial carbons.

FIG. 3 represents the structure of the partially esterified TA lipid ($P^1$:$P^2$:$P^3$:$P^4$=COOH OR $COOR^1$) of example 2. Carbons $C_{17'}$ and $C_{17'''}$ (circle)

FIG. 4 represents (FIG. 4A) a Tetra-acidosome of the present invention with natural TA lipids (encircled TA lipid) (FIG. 4B) the detailed structure of the main TA lipids present in large quantities in petroleum calcium naphthenate deposits (=industrial waste product).

EXAMPLES

Material and Methods

Figure 5:
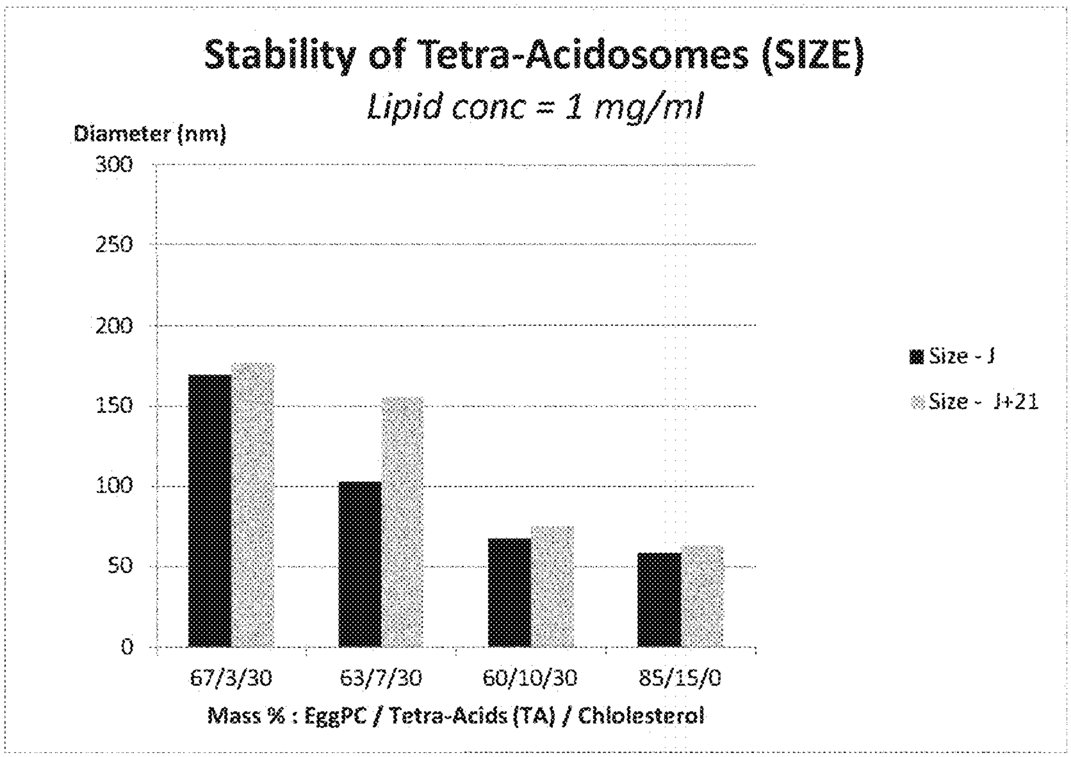
FIG. 5 represents the stability of Tetra-acidosomes of the present invention in terms of size.

General: $^1$H NMR spectra were recorded on a Bruker Avance III 400 spectrometer operating at 400.13 MHz for, equipped with a BBFO probe with a Z-gradient coil and a GREAT 1/10 gradient unit. All experiments were carried out at 25° C.

The noesygppr1d Bruker pulse program was used for 1D NMR with presaturation using the following parameters: TD of 64k, a relaxation delay d1=2 s and 16 scans. The spectrum width was set to 18 ppm. Fourier transform of the acquired FID was performed without any apodization in most of the case.

$^{13}$C NMR spectra were recorded at 100.61 MHz. Several sequences as jmod, dept135 or zgpg30 were usually used with 64 to 1024 scans depending on the concentration of the sample. TD is 64k and a relaxation delay of 2 s for a spectral width of 220 ppm was used. Fourier transform was performed after apodization with an exponential function using a LB of 0.6 Hz.

Concerning, mass spectrometry analyses, SI+, ESI− and MALDI ionisation were used.

All the reagents were brought from known providers like Merck, Fischer and Alfa Aesar and were used without purification.

General Procedures for Formulation:

Procedure A: 4 mg·mL$^{-1}$ stock solutions of EggPC, cholesterol and lipids were prepared in MeOH (HPLC grade) and $CHCl_3$ (HPLC grade) (depending on solubility). The solutions were placed under ultrasounds for 5 mins to be certain that all lipids were well dissolved. The formulations were then prepared in 1 mL depending on the chosen mass %. Operatory conditions for NanoAssemblr® were selected in a software.

Example

Volume: 3.3 mL
FRR: 3:11
TFR: 8 $mL \cdot min^{-1}$
Left syringe: aqueous phase—3 mL syringe (dispense: 2.47 mL)
Right syringe: organic phase—1 mL syringe (dispense: 0.83 mL)
Star waste volume: 0.350 mL
End waste volume: 0.050 mL The aqueous phase is Dulbecco's Phosphate-Buffered Saline (DPBS). The organic phase was extracted with rotavapor: 2×1000 μL of the liposomal solution were placed in a 10 mL flask, itself placed in 40° C. bath; Pressure was set at 300 mbar during 10 min, then it was lowered by 20 mbar every 20 s until 100 mbar was reached, and it was maintained at 100 mbar 5 additional minutes. The formulation was recovered with a syringe and was sterilized with Acrodisc, then the mass was adjusted to 2 g with DPBS. Theoretical final concentration was 1 $mg \cdot L^{-1}$. Each formulation was analysed by DLS with Zetasizer Malvern ZS90: 3 measures by sample corresponding to 10 runs of 20 s with 90 s of equilibration at the beginning. Temperature was set at 25° C.

Procedure B: 4 $mg \cdot mL^{-1}$ stock solutions of EggPC, cholesterol and lipids were prepared in EtOH (HPLC grade). The solutions were placed under ultrasounds for 5 mins to be certain that all lipids were well dissolved. The formulations were then prepared in 1 mL depending on the chosen molar %. Operatory conditions for NanoAssemblr® were selected in a software.

Example

Volume: 2.4 mL
FRR: 3:11
TFR: 12 $mL \cdot min^{-1}$
Left syringe: aqueous phase—3 mL syringe (dispense: 1.8 mL)
Right syringe: organic phase—1 mL syringe (dispense: 0.6 mL)
Star waste volume: 0.350 mL
End waste volume: 0.050 mL The aqueous phase is Dulbecco's Phosphate-Buffered Saline (DPBS). The organic phase (EtOH) was removed by dialysis: 1000 μL of the liposomal solution were placed in a 1 mL hydrated dialysis tube (Spectrum Laboratories G235035, cut-off=100 kDa) and the filled tube was then placed in 250 mL of milliQ water with magnetic stirring at 350 rpm. The milliQ water bath was changed after one hour. 500 μL of the liposomal solution inside the dialysis tube was analysed by DLS with Zetasizer Malvern ZS90: 3 measures by sample corresponding to 10 runs of 20 s with 90 s of equilibration at the beginning. Temperature was set at 25° C.

Example 1: Synthesis of Tetraol Lipid ($P^1$=$P^2$=$P^3$=$P^4$=$CH_2OH$)

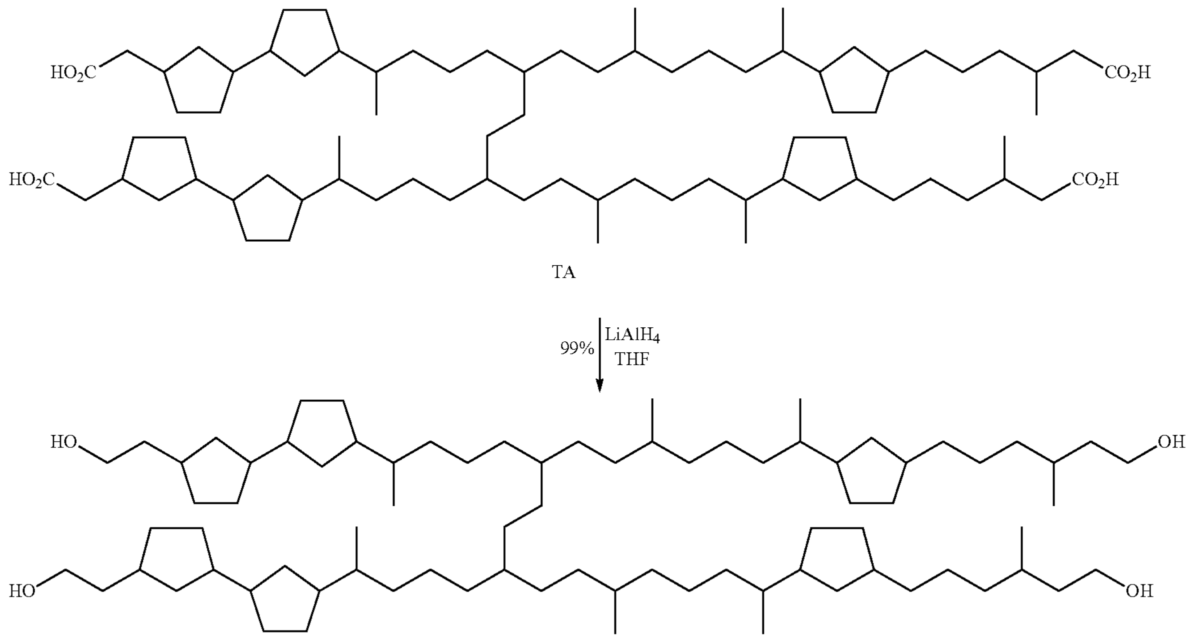

TA

Tetraol

Scheme 1: Synthesis of Tetraol Lipid Derived from TA Lipid $LiAlH_4$ (19.5 mg, $5.13 \cdot 10^{-4}$ mol, 6 equiv.) used as reducing agent was dissolved in 8 mL of anhydrous THF. TA lipid (95.8 mg, $7.78 \cdot 10^{-5}$ mol, 1 equiv) dissolved in 4 mL of anhydrous THF were added dropwise under inert atmosphere. The resulting mixture was then stirred at reflux for 5 h. Excess $LiAlH_4$ was destroyed by addition of 6 mL of diethyl ether then 3 mL of water. The aqueous phase was extracted with diethyl ether, then the gathered organic phases were washed with sulfuric acid 5% in water and water. After drying with $MgSO_4$, the solvent was removed under reduced pressure to obtain a yellow oil (90.2 mg, 99% yield). $^1H$ NMR in $CDCl_3$: δ=2.3-1.5 (m), 1.4-1.0 (m), 0.91

(d, J=6.5 Hz), 0.89-0.83 (m), 13C NMR in $CDCl_3$: 62.4, 61.2, 46.5, 45.7, 45.1, 44.9, 44.8, 39.9, 39.5, 39.4, 39.1, 38.3, 37.9, 37.3, 37.2, 36.6, 36.1, 35.7, 34.7, 34.1, 33.7, 33.3, 33.2, 31.9, 31.7, 31.5, 31.2, 30.3, 29.7, 29.6, 29.3, 29.2, 25.9, 25.7, 24.4, 24.1, 22.7, 19.9, 19.6, 17.8, 14.1.

Complete reduction of the four carboxylic acids into primary alcohol functions was fulfilled in a quasi-quantitative yield. 1D NMR spectra proved that the tetraol was obtained as the signals of the carboxyl acid carbons are not present anymore and two signals corresponding to the hydroxyl functions appeared at 61.23 ppm and 62.43 ppm on the 1 D $^{13}C$ spectrum. Also, a general shielding of the aliphatic protons is observed on the 1D $^{1}H$ spectrum, especially the doublet at 0.91 ppm which was at 0.98 ppm for the initial TA lipid. The synthesis was also confirmed by high resolution mass spectrometry since the peak for m/z 1175 was found.

Example 2: Synthesis of Partially Esterified TA Lipid (at Least One $P^1$:$P^2$:$P^3$:$P^4$=$COOR^1$)

interaction with the resin was reduced. Several experiments were carried out by changing reaction time or solvent ratio. The results are shown in Table 1 below with estimated total esterification rates and esterification rates of the right and left sides calculated depending on the time of reaction or solvent ratio.

Three signals in the $^{1}H$ NMR spectrum allowed the calculation of both the global esterification rate and the esterification rate of the right side of the lipid. The doublet found at 0.94 ppm and the doublet at 0.98 ppm correspond to the $CH_3$ of carbons $C_{17'}$ and $C_{17'''}$ (FIG. 3). If the polar head is a carboxylic acid, the doublet is found at 0.98 ppm whereas if it is a butyl ester, the doublet is found at 0.94 ppm. However, a triplet corresponding to the terminal $CH_3$ of the butyl ester was found at 0.95 ppm and was superimposed with the doublet at 0.94 ppm. With a line fitting of the region between 1.01 and 0.92 ppm, it was possible to integrate separately the three signals.

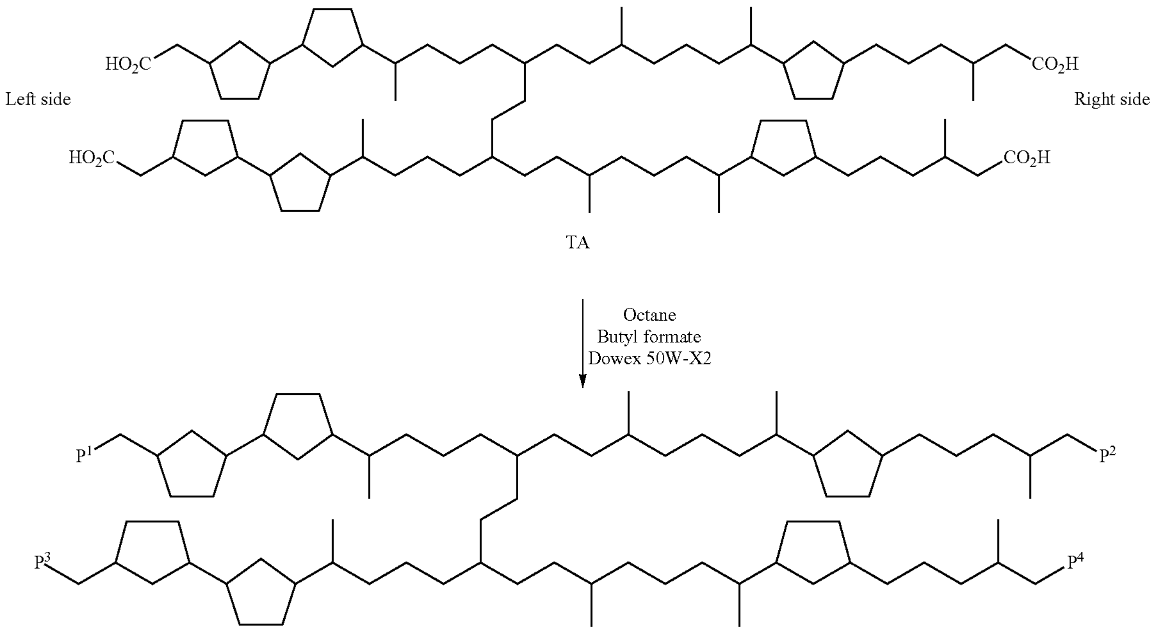

Partially esterified TA $P^1$, $P^2$, $P^3$, $P^4$ = COOH
or
COO—$(CH_2)_3$—$CH_3$ Scheme 2: Selective Esterification of a TA Lipid Using an Acidic Resin The selective esterification of a TA lipid was performed through the use of an acidic resin. The TA lipid was dissolved in a large excess of a mixture of octane and butyl formate, and a reaction of transesterification occured at the interface of a strongly acidic ion-exchange resin which is Dowex 50W-X2 (50-100 mesh). The explanation for the selectivity was based on the great solubility of tetracarboxylic acid (TA) lipids in butyl formate compared to octane. The transesterification occured at the resin and butyl formate interface due to the acidic aqueous characteristic of the resin. Then, the resulting partially esterified TA lipid, which is far more soluble in octane, has not been as reactive and its There is a mathematical relationship between the integration of these three signals. As each $C_{17'}$ and $C_{17'''}$ (FIG. 3) always correspond to $CH_3$, the sum of the integration of the two doublets is always equal to 6. As for the triplet, its integration can range between 0 and 12 protons since a lipid can possess between 0 and 4 butyl ester functions, i.e. between 0 and 4 terminal $CH_3$ of butyl esters. With a cross product, it is possible to determine the integration of the triplet and compare it with the theoretical maximum, which is 12, i.e. global esterification rate=$(\text{integration}_{triplet0.95ppm}/12)*100$. The esterification rate of only the right side of the molecule is given by $(\text{integration}_{doublet0.94ppm}/6)*100$.

TABLE 1

| Entry | Solvent ratio ($n_1/n_2$) | Reaction time (h) | Estimated esterification rate (%) | Estimated esterification on the right side (%) | Deduced esterification on the left side (%) |
|---|---|---|---|---|---|
| 1 | 90/10 | 2 | 3 | 0 | 6 |
| 2 | 90/10 | 6 | 8 | 0 | 16 |
| 3 | 90/10 | 14 | 11 | 3 | 19 |
| 4 | 90/10 | 24 | 12 | 4 | 22 |
| 5 | 90/10 | 72 | 61 | 20 | 100 |
| 6* | 50/50 | 24 | 57 | 14 | 100 |
| 7 | 50/50 | 120 | 84 | 73 | 100 |

*After silica gel column chromatography, a fraction was isolated with a total esterification rate of 51%, an esterification rate of 5% at the right side and an esterification rate of 97% at the left side.
$n_1$ = octane; $n_2$ = butyl formate.

Entries 1-5 in Table 1 gave information on the reaction time needed to transform the carboxylic acids into butyl esters with a 90/10 solvent ratio. Within 24 h, the conversion was limited as only 13% was reached. It was still possible to get satisfactory conversion rate since 61% was reached after 3 days (entry 5). Then, the effect of solvent ratio was important. The esterification rate has been multiplied by 4.5 for the same reaction time, by increasing the proportion of butyl formate (entry 4 and entry 6). It was possible to almost convert the carboxylic acids completely into butyl esters after a longer reaction time and with enough butyl formate (entry 7). In addition, the esterification was selective for all the conditions that were tested (entries 1-7). Indeed, the esterification rate for the right side of the molecule increased slowly compared to the global esterification. Therefore, the conditions of this reaction have been optimised to obtain TA lipids with the number of ester functions controlled, with the left side of the lipids more substituted than the right side. Indeed, the more the reaction time increased, the more tetraesters were obtained. This means that after a certain time, the difference in solubility in octane and butyl formate was not enough to prevent the reaction from continuing. Also, it was not clear why the left part of the molecule appeared to be more reactive for this reaction. It may be due to the geometry of approach of the lipids towards the resin which could be more favourable for one side of the molecule.

In conclusion, a 50/50 solvent ratio and a reaction time of 24 h (entry 6) were the most appropriate conditions for an asymmetrical esterification of TA lipids since the esterification rate at the right side was low (14%) compared to the left side (100%). Furthermore, the removal of the tetraester compound (Fraction 1) by column chromatography allowed to isolate partially esterified TA lipids (Fraction 2) with total esterification rate of 51%, an esterification rate of 5% at the right side and an esterification rate of 97% at the left side (see below).

Representative Reaction for Partial Esterification of TA Lipid:

TA lipids (107 mg, 0.086 mmol, 1 equiv.) were dissolved in 20 mL of a 50/50 mixture of octane and butyl formate. Dowex 50W-X2 (50-100 mesh) (500 mg) was added, and the mixture was stirred at 100° C. for 24 h. The resin was eliminated by filtration. The solvent was removed under reduced pressure to obtain a yellow oil (114 mg). Two fractions were isolated after flash chromatography ($CH_2Cl_2$/MeOH: 100/0 to 90/10). Fraction 1 (10 mg) was identified as tetrabutylester ($P_1$=$P_2$=$P_3$=$P_4$=$CO_2Bu$), fraction 2 (83 mg, 72%) was composed of partially esterified TA lipids (total esterification rate: 51%; esterification rate of 5% at the right side and esterification rate of 97% at the left side). $^1H$ NMR in $CDCl_3$: Fraction 1, same as tetraester: 4.08 (8H, 2t, J=6.7 Hz), 2.37-2.05 (10H, m), 1.95 (4H, m), 1.76 (10H, m), 1.61 (14H, m), 1.5-1.0 (80H, m), 0.95 (12H, t, J=7.2 Hz), 0.94 (6H, d, J=7.2 Hz), 0.86 (20H, m); Fraction 2: 4.08 (2H, 2t, J=6.7 Hz), 2.4-1.9 (14H, m), 1.9-1.5 (20H, m), 1.4-1.0 (80H, m), 0.98 (6H, d, J=7.0 Hz), 0.95 (6H, t, J=7.1 Hz), 0.9-0.7 (20H, m).

Example 3: Total or Partial Pegylation of a TA Lipid (at Least One $P^1$:$P^2$:$P^3$:$P^4$=$A^2$-$(PEG_{x1}$-$A^3)$n-$R^2$ OR $COOR^1$)

The goal here was to introduce PEG chains on the lipids to give mucus-inert properties to Tetra-acidosomes. The strategy of PEGylation was based on peptide coupling reactions between the carboxylic acids of the lipid and the amine of the PEG. TBTU (2-(1H-Benzotriazole-1-yl)-1,1,3,3-tetramethylaminium tetrafluoroborate) and DIPEA (N—N-diisopropylethylamine) were selected since they are known for their efficiency in coupling reactions with other lipids [19]. The use of a uronium salt like TBTU allowed by itself the formation of HOBt (1-Hydroxybenzotriazole hydrate) while DIPEA ensured that the carboxylic acids were deprotonated. Also, to avoid the formation of secondary products, the amine was added after at least 20 min of stirring of the TA lipid with TBTU and DIPEA so that the carboxylate functions were completely activated as esters of HOBt.

Synthesis of tetrazidoPEGylated $(N_3PEG_{500})_4$-TA Lipids using $N_3$-$PEG_{500}$-$NH_2$ The first coupling reaction was performed between $N_3$-$PEG_{500}$-$NH_2$ and the initial TA lipid to obtain tetrazidoPEGylated $(N_3PEG_{500})_4$-TA lipid (scheme 3) that would serve in the copper catalysed cycloaddition described in the next part related to the functionalization of PEG chains (scheme 5).

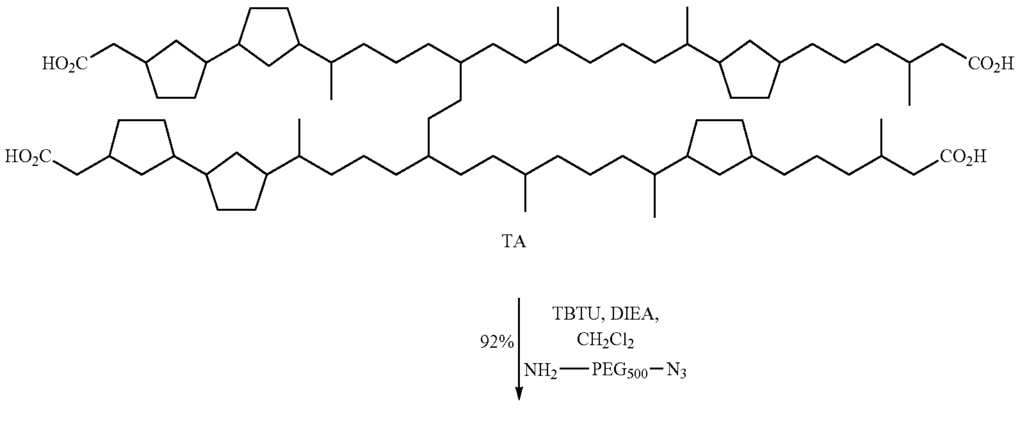

TA

-continued

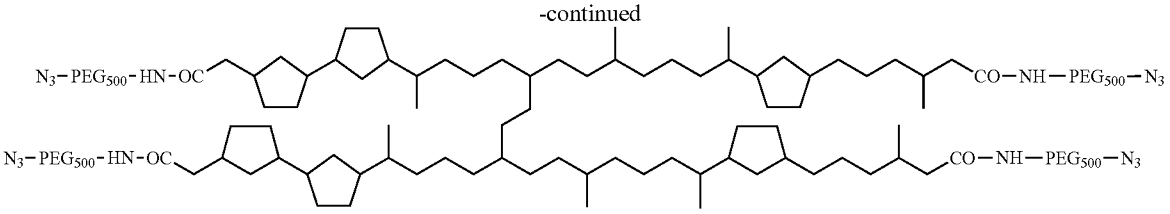

$(N_3PEG_{500})_4$—TA

Scheme 3: Synthesis of the tetrazidoPEGytated ($N_3$ PEG)$_4$-TA lipid with $N_3$-$PEG_{500}$-$NH_2$ TBTU (75 mg, 0.23 mmol, 4.8 equiv.), DIPEA (4.8 equiv.) and TA lipids (60 mg, 0.049 mmol, 1 equiv.) were dissolved in 9 ml of anhydrous $CH_2Cl_2$ under inert atmosphere. DIPEA (30 mg, 0.23 mmol, 4.8 equiv) was added in the mixture. After 20 minutes, $N_3$-$PEG_{500}$-$NH_2$ (102 mg, 0.23 mmol, 4.8 equiv.) dissolved in 3 mL of anhydrous $CH_2Cl_2$ was added, and the mixture was brought to reflux for 48 h. Then, DIPEA was neutralized by adding some drops of 4% HCl solution. The organic phase was washed with distilled water (3×2 mL). The organic phase was dried with $MgSO_4$. The solvent was removed under reduced pressure and the crude product was purified by flash chromatography ($CH_2Cl_2$/MeOH:100/0 to 90/0) to obtain a tetrazidoPEGylated ($N_3PEG_{500}$)$_4$-TA lipid as a yellow oil in excellent yield (92%). $^1$H NMR in $CDCl_3$: δ=3.8-3.2 (160H, m, HPEG), 2.1 (6H, m), 1.9 (6H, m), 1.8-1.59 (16H, m), 1.4-0.9 (78H, m), 0.85 (6H, d, J=6.2 Hz), 0.78 (16H, m). The $^1$H NMR spectrum confirmed the structure as integrations are correct, and a shielding resulting from the formation of amides is observed and is more important for protons located near these amides.

Representative PEGylation of a Partially Esterified TA Lipid Using MeO-$PEG_{2000}$-$NH_2$ In addition, partially esterified TA lipids (46%) with known esterification rate were then engaged in the coupling reaction but with MeO-$PEG_{2000}$-$NH_2$.

Scheme 4: Synthesis of the Partially Esterfied TA with MeO-$PEG_n$-$NH_2$.

Figure 7:
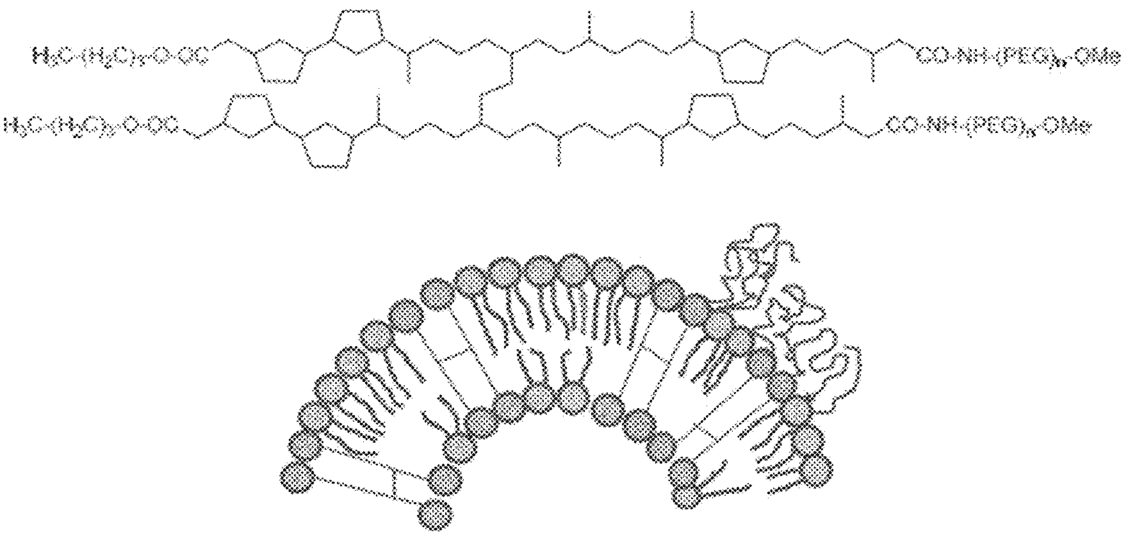
FIG. 7 represents PEGylation of TA lipids: asymmetrical introduction to prevent the chains from potentially filling the hydrophilic heart of Tetra-acidosomes.
Figure 8:
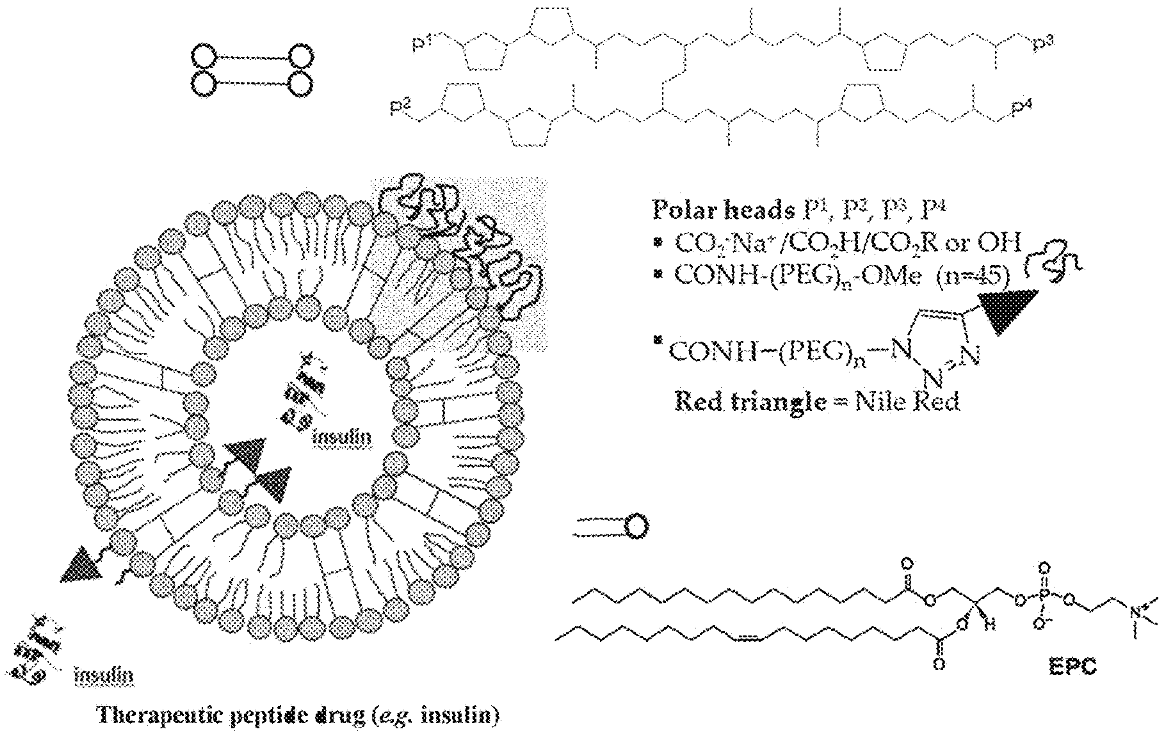
FIG. 8 represents the structure of a peptide loaded Tetra-acidosome composed of TA (with different polar heads), fluorescent labelled TA (Nile Red TA) and PEGylated TA lipids.

Partially esterified TA lipids (see Fraction 2 of Example 2) (10 mg, 0.008 mmol, 1 equiv.), TBTU (6.2 mg, 0.019 mmol, 2.4 equiv: 1.2 equiv. for each equiv. of carboxylic acids) were dissolved in 2 mL of anhydrous $CH_2Cl_2$ under inert atmosphere. DIPEA (6.7 mg, 0.019 mmol, 2.4 equiv: 1.2 equiv. for each equiv. of carboxylic acids) was added in the mixture. After 20 minutes, MeO-$PEG_{2000}$-$NH_2$ (38 mg, 0.019 mmol, 2.4 equiv: 1.2 equiv. for each equiv. of carboxylic acids) dissolved in 5 mL of anhydrous $CH_2Cl_2$ was added and the mixture was brought to reflux for 48 h. Then, DIPEA was neutralized by adding some drops of 4% HCl solution. The organic phase was washed with distilled water (3×2 mL). The organic phase was dried with $MgSO_4$. The solvent was removed under reduced pressure and the crude product was purified by flash chromatography ($CH_2Cl_2$/MeOH: 100/0 to 90/0) to obtain a yellow oil (42 mg). $^1$H NMR in $CDCl_3$: δ=3.8-3.2 (HPEG), 2.4-1.9 (m), 1.9-1.4 (m), 1.4-0.95, 0.95-0.70 (m). NMR spectra proved that the remaining carboxylic acids of the TA lipids are quasi quantitively PEGylated. The initial goal of controlling where the PEG chains are grafted to the TA lipids could then be achieved in excellent yield with prior selective protection of the right carboxylic acids (FIG. 7).

Thereafter, to confirm that previous selective esterification of the TA lipids is necessary to obtain diPEGylated lipid

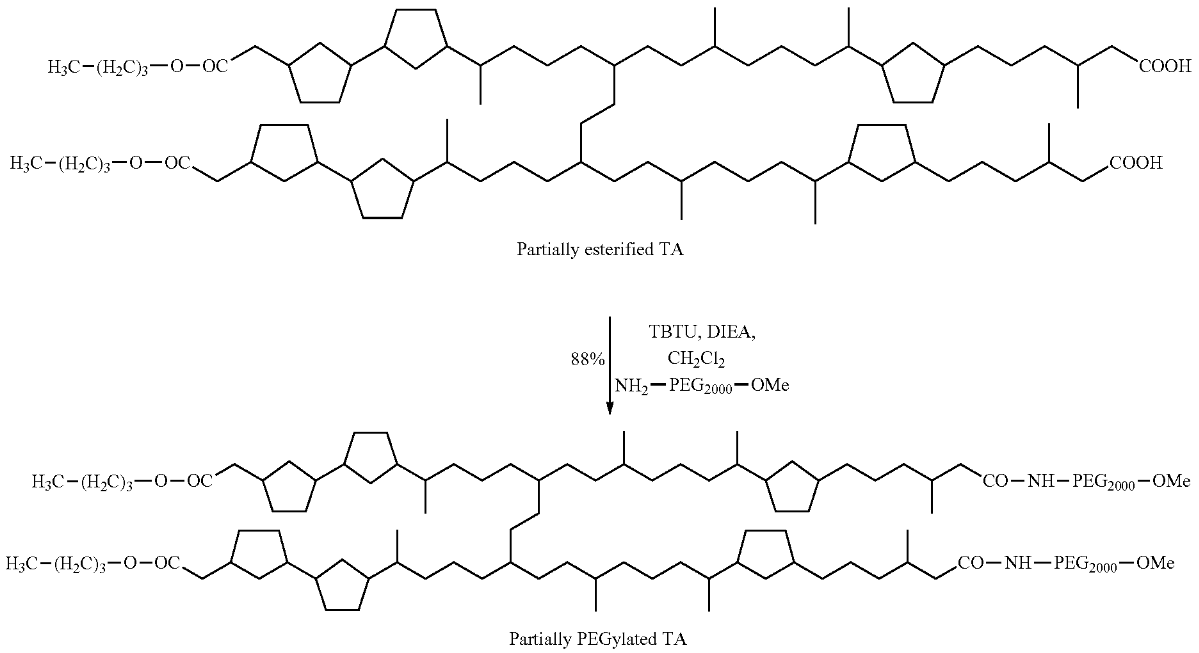

Partially esterified TA

Partially PEGylated TA with PEG chains on the same side of the molecule, a coupling reaction with (non-protected) initial TA lipids was performed. TBTU (2 equiv.), DIPEA (2 equiv.) and TA lipids (1 equiv.) were added in anhydrous $CH_2Cl_2$, before adding MeO-$PEG_{2000}$-$NH_2$ (2 equiv.). We got diPEGylated TA lipids in a quasi-quantitative yield but integrations on the $^1H$ NMR spectrum showed that the PEG chains were statistically attached to the right or left part of the lipids. Thus the way to control where the PEG chains will be attached is to protect selectively the carboxylic acids beforehand, as previously described.

Example 4: Functionalization of the Pegylated TA Lipids ($P^1$:$P^2$:$P^3$:$P^4$=$A^2$-($PEG_{X1}$-$A^3$)$_n$-$R^2$ OR $COOR^1$)

The introduction of a specific function (targeting agent, probe) at the terminal ends of the PEG chains could be achieved through esterification reactions, peptidic coupling reactions or click chemistry reactions (for example using Copper catalysed Huisgen cycloaddition). As an example, the introduction of a probe at the four terminal ends of the tetrazidoPEGylated ($N_3PEG_{500}$)$_4$-TA lipids was performed for biopharmaceutical characterizations. Copper catalysed Huisgen cycloaddition is now popular to easily add probes or specific molecules to lipids for example. However, it is fundamental to find the right conditions, i.e. right solvent and catalyst, as yields can easily drop. Classically, copper sulphate with ascorbic acid as additive are used in polar solvents like water or alcohols.

Given the aliphatic structure of TA lipids, it looked relevant to try the reaction with other conditions.

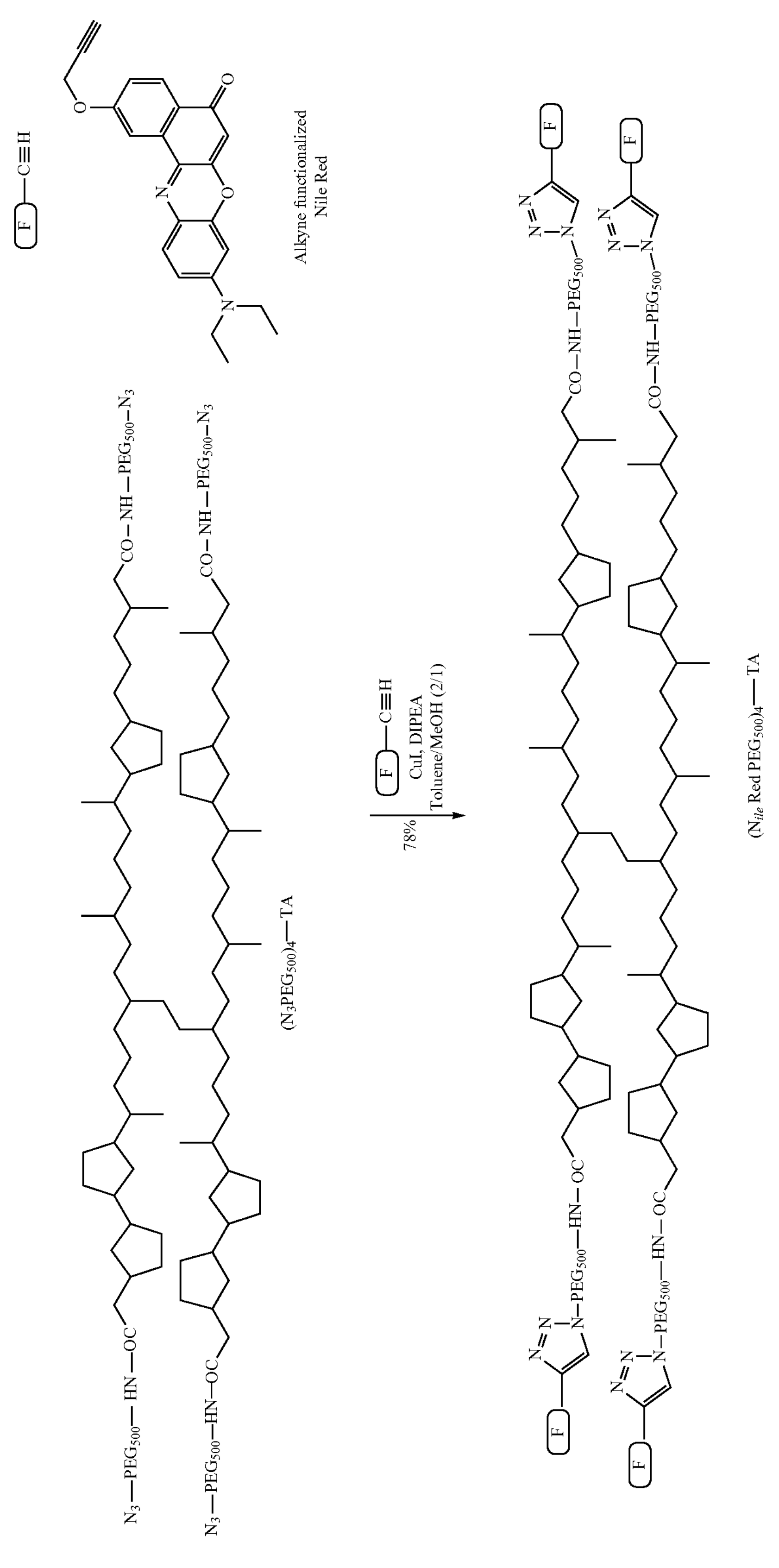
Alkyne functionalized Nile Red
$(N_3PEG_{500})_4$—TA
$(N_{ile}\ Red\ PEG_{500})_4$—TA Scheme 5: Synthesis of the Nile Red Labelled tetraPEGylated (Nile Red-$PEG_{500}$)$_4$-TA Lipids by Click Reaction TetrazidoPEGylated ($N_3PEG_{500}$)$_4$-TA lipids (50 mg, 61.9 mmol, 1 equiv.) and 9-diethylamino-2-(prop-2-ynyloxy)-5H-benzo[α]phenoxazine-5-one (Nile Red probe [20]: 23 mg, 61.9 mmol, 4 equiv.) were dissolved in a mixture of 9 mL of two organic solvents: anhydrous toluene and anhydrous methanol (MeOH) in a 2/1 ratio (scheme 5). The catalyst copper iodide (CuI) which is directly at an oxidation degree of I (13.6 mg, 40% mol) was added, followed by DIPEA, and the reaction mixture was stirred at 60° C. overnight. The mixture was cooled and filtered, and the filtrate was concentrated under reduced pressure. The residue was purified by flash chromatography ($CH_2Cl_2$/MeOH: 100/0 to 90/0) to obtain a dark purple oil (57 mg, 78%) corresponding to the tetra-Nile-Red functionalized (Nile Red-$PEG_{500}$)$_4$-TA lipid. $^1$H NMR in $CDCl_3$: δ=8.2 (8H, m), 7.97 (s, 4H), 7.59 (4H, m), 7.24 (4H, m), 6.65 (4H, m), 6.44 (4H, m), 6.29 (4H, m), 4.6 (8H, m), 3.9-3.3 (145H, HPEG), 2.3-1.8 (34H, m), 1.73 (6H, m), 1.63 (8H, m), 1.55-0.96 (100, m), 0.91 (6H, m), 0.83 (12H, m). The formation of triazoles was evidenced in $^1$H NMR by the presence of a singlet at 7.9 ppm corresponding to 4 protons, and the loss of the signal at 2.58 ppm of the alkynes.

Example 5: Functionalization of the TA Lipids with Cationic Moieties or with Butanol Functionalization of the TA Lipids with Choline ($P^1$:$P^2$:$P^3$:$P^4$=$A_1$-$CH_2$—$CH_2$—$N^+(CH_3)_3$, $X^-$ with X═Cl)

Esterification of the TA lipids was achieved in quasi quantitative yield using MSA as catalyst in a two-step reaction.

Scheme 6: Synthesis of Tetracholine Ester Lipids Derived from TA Lipids

Firstly, choline chloride (27 mg, 0.19 mmol, 4.8 equiv.) was put in a flask with a Dean-Stark under inert atmosphere. Then MSA (20 mg, 0.21 mmol, 5.0 equiv.) was added and the mixture was stirred for 30 min. During this first step, the counter ion of the choline became mesylate while HCl was released.

The second step was the esterification using the hydroxyle function of choline in acidic conditions and at a temperature of 130° C. TA lipids 1 (50 mg, 0.040 mmol, 1 equiv.) dissolved in anhydrous toluene was added and the temperature was set at 130° C. The mixture was stirred overnight then the solvent was removed under reduced pressure. 90 mg (112%) of the crude product was obtained. $^1$H NMR in $CDCl_3$/$CD_3OD$ (50/50): 4.02 (8H, m), 3.5 (8H, m), 3.2 (36H, s), 2.4-1.5 (28H, m), 1.4-1.0 (58H, m), 0.94 (6H, d, J=0.93 Hz), 0.9-0.6 (16H, m). 1 D H NMR spectrum confirmed that the expected tetraester was obtained as the signal of the alcohol disappears and the formation of the ester function caused a change of chemical shifts for the protons of TA lipids.

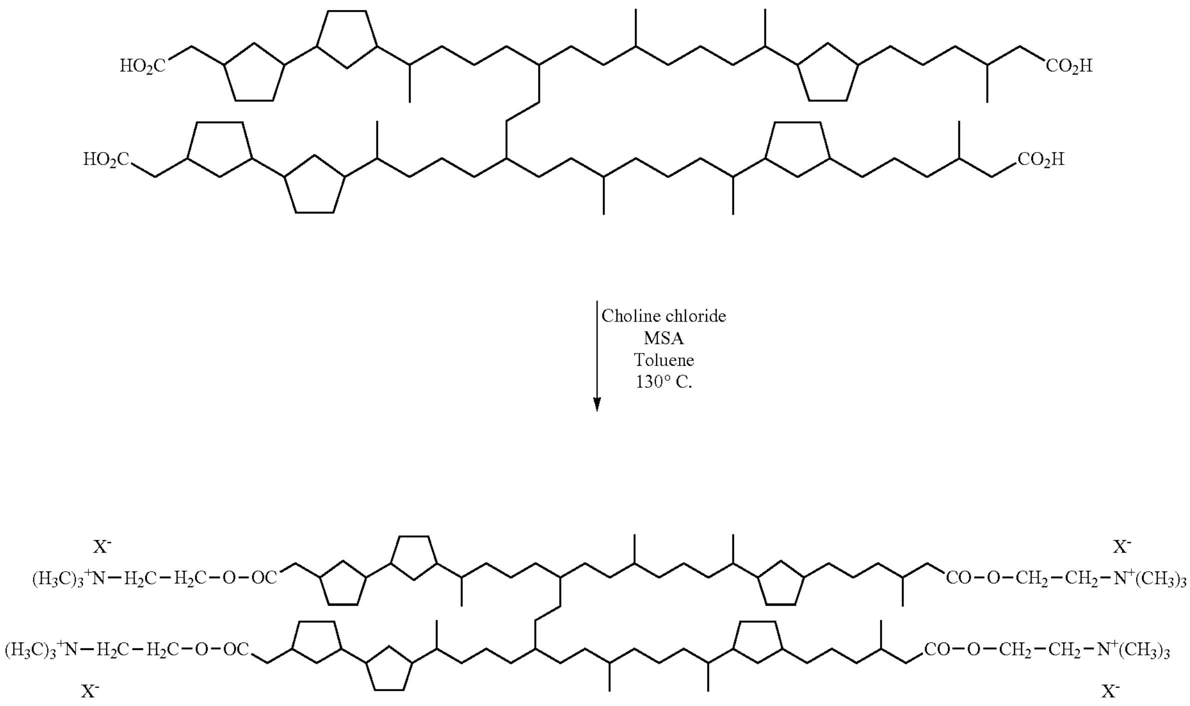

Functionalization of the TA Lipids with BUTANOL ($P^1$:$P^2$:$P^3$:$P^4$=$CO_2$—$(CH_2)_3$—$CH_3$)

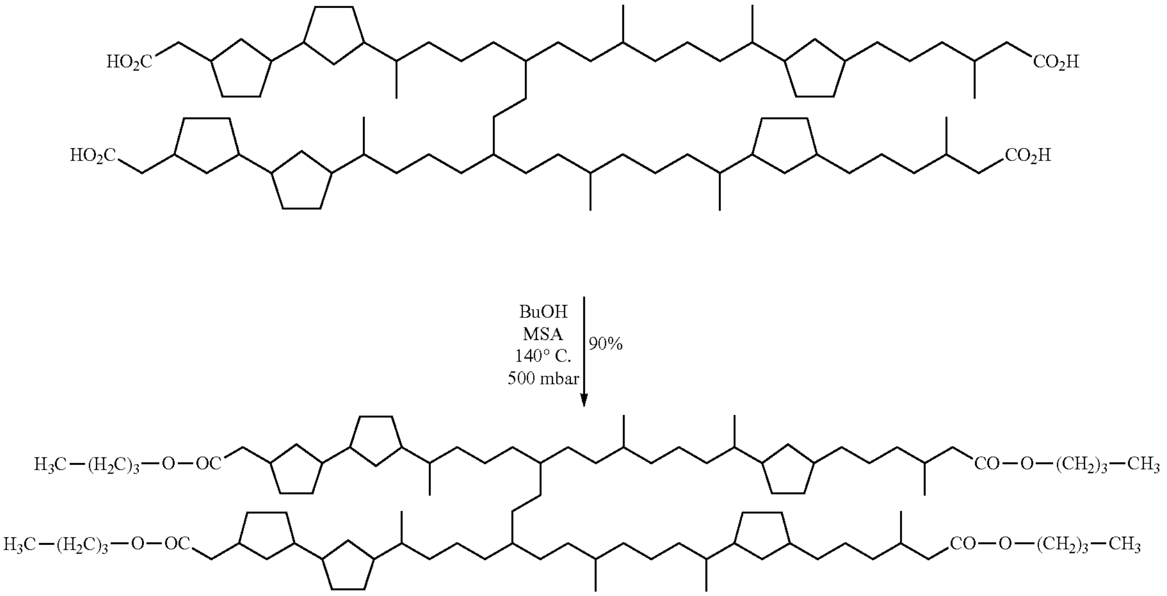

Scheme 7 Synthesis of Tetrabutyl Ester Lipids Derived from TA Lipids

Fisher esterification was envisaged to synthesize tetraester. TA lipids (26.3 mg, 2.14.10-5 mol, 1 equiv.) was dissolved in 5 mL of n-butanol (nBuOH) used both as nucleophillic ragent and solvent. Methane sulfonic acid (MSA, 125 μL, 0.1 equiv.) used as acidic catalyst was added, then the mixture was stirred at 140° C. in a flask with Dean-Stark apparatus to eliminate water formed during the reaction. The pressure was set at 500 mbar. After 7 h, the solvent was removed under reduced pressure to obtain a yellow oil. $^1$H NMR in $CDCl_3$: δ=4.08 (8H, 2t, J=6.7 Hz), 2.37-2.05 (10H, m), 1.95 (4H, m), 1.76 (10H, m), 1.61 (14H, m), 1.5-1.0 (80H, m), 0.95 (12H, t, J=7.2 Hz), 0.94 (6H, d, J=7.2 Hz), 0.86 (20H, m), $^{13}$C NMR in $CDCl_3$: 171.0, 170.98, 67.3, 61.5, 60.3, 50.9, 43.8, 43.0, 42.7, 42.2, 39.4, 38.3, 36.4, 35.8, 35.4, 35.0, 34.8, 34.4, 34.0, 33.5, 32.3, 32.2, 31.5, 31.2, 30.8, 30.6, 30.0, 29.9, 28.7, 28.5, 28.1, 27.8, 27.2, 23.3, 21.9, 21.5, 20.1, 17.4, 17.2, 16.6, 16.3, 16.1, 15.2, 11.2. Tetraester was isolated in a 90% yield. NMR experiments confirmed that all carboxylic acids were transformed into butyl esters.

Example 6: Formulation of Natural Tetra-Acids (TA) Lipids or Chemically Functionalized Tetra-Acids (CFTA) Lipids into Stable Liposomes Called Tetra-Acidosomes The classic method to formulate liposomes is to form a lipid film by solvent evaporation which is then hydrated with an aqueous solution and sonicated. This method can work but is not the most convenient and reproducible one. An interesting alternative exists which is microfluidics. Development of new continuous processes to elaborate matrix particles is burgeoning. Microfluidics is the science which studies the manipulation of small volumes (from $10^{-9}$ to $10^{-18}$ L) in microscopic canals (from 10 to 1000 μm). Microfluidics is a very efficient tool to formulate liposomes and it is performed in the examples given hereafter thanks to an equipment called NanoAssemblr® Benchtop. It offers reproducibility, tuning of particle sizes, scalability, and speed. All the results presented below were obtained using this platform. Ideally, liposomes with diameters lower than 200 nm and with Polydispersity Index (PDI) lower than 0.3 are required to consider that the formulations are suitable for encapsulation of molecules. These two parameters are provided by Dynamic Light Scattering (DLS). The PDI is a dimensionless measure of the broadness of the particle size distribution, and it ranges from 0 to 1. If its value exceeds 1, it may be that the sample is not suitable for measurement by DLS.

Formulations Based on Natural TA Lipids (Procedure A)

Several formulations were tested using TA or PEGylated TA, EggPC and cholesterol with well-defined mass percentages and some of them are presented in Table 2.

TABLE 2

Composition of the different organic solutions prepared for formulations of Tetra-Acidosomes

| Formulation name | mass % of EggPC | mass % of TA | mass % of cholesterol |
|---|---|---|---|
| A | 67 | 3 | 30 |
| B | 63 | 7 | 30 |
| C | 60 | 10 | 30 |
| D | 85 | 15 | 0 |

Cholesterol can be associated with the two other lipids to modulate the rigidity of the layer. The organic phase was constituted of MeOH as TA lipids were soluble enough to get stock solutions of 4 mg·$L^{-1}$. Once the formulations were produced, the organic phase was evaporated, and the liposomal solutions was diluted to get precisely two grams of solution of theorical concentration of 1 mg·$mL^{-1}$. They were then analysed by DLS to get the Z-average in nm and the PDI (Table 3).

TABLE 3

| Z-average (nm) and PDI measured by DLS for the Tetra-Acidosomes formulations with natural TA lipids at J and J + 21 days | | | | |
|---|---|---|---|---|
| Formulation name | A | B | C | D |
| Average size (nm) - J | 169.5 | 102.9 | 67.6 | 58.7 |
| Average size (nm) - J + 21 | 177.0 | 156.2 | 75.4 | 63.6 |
| Average PDI - J | 0.042 | 0.059 | 0.047 | 0.05 |
| Average PDI - J + 21 | 0.046 | 0.095 | 0.062 | 0.034 |

Firstly, liposomal solutions made from TA lipids associated with EggPC and/or cholesterol were obtained with hydrodynamic diameters lower than 200 nm. Moreover, the PDI for each formulation is excellent as it is always inferior to 0.1, which means that we were able to formulate monodisperse lipidic vesicles. Secondly, it was observed that the more the concentration of TA lipid increased, the more the hydrodynamic diameter decreased. Then, the diameter of the liposomes can be controlled by varying the mass percentage of TA lipids. More interestingly, these formulations were very stable. Indeed, after twenty-one days, the average diameters and PDIs of the formulations remained almost unchanged.

FIGS. 4A-4B illustrate the structure of a Tetra-acidosome of the present invention with natural TA lipids.

Figure 6:
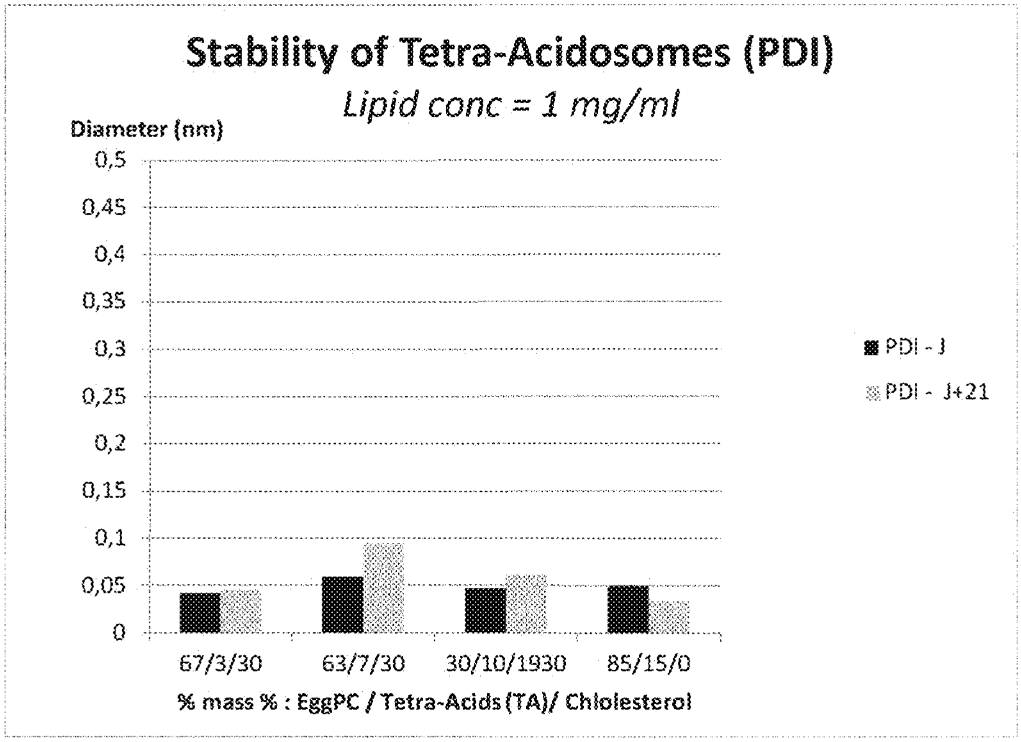
FIG. 6 represents the stability of Tetra-acidosomes of the present invention in terms of PDI (PolyDispersity Index).

FIGS. 5 and 6 illustrate the stability of Tetra-acidosomes of the present invention with natural TA lipids in terms of size and PDI, respectively.

Formulations Based on Tetraol Lipids (Procedure A)

Four formulations were tested with tetraol with the same mass percentages as solutions A, B, C and D. Some differences that could be noted from TA lipids-containing liposomes. The tetraol lipids are not soluble in MeOH so the organic phase was constituted of a mixture of MeOH and $CHCl_3$ 1/1. A turbidity appeared when the mass percentage of tetraol was equal or superior to 10 wt. %. The four formulations were also analysed by DLS (Table 4).

TABLE 4

| Z-average (nm) and PDI measured by DLS for the formulations of Tetra-acidosomes with tetraol 2. | | | | |
|---|---|---|---|---|
| Formulation name | A | B | C | D |
| Average size (nm) | 153.1 | 104.4 | 149.2 | 130.8 |
| Average PDI | 0.067 | 0.085 | 0.076 | 0.172 |

Some interesting formulations were obtained with diameters lower than 200 nm and good PDIs. However, there are some differences to mention. The hydrodynamic diameter did not decrease anymore as the mass percentage of tetraol increased. Cholesterol-containing liposomes showed excellent PDIs, but the formulation D, which only contained tetraol and EggPC, has a PDI value higher than 0.1, even though it can still be considered acceptable as it is lower than 0.3. Also, liposomes with diameters lower than 100 nm were not obtained.

Comparative Formulations Based on Natural TA Lipids or Partially PEGylated TA Lipids (Procedure B)

Several formulations were tested using TA lipids or partially PEGylated TA lipids, EggPC and cholesterol with well-defined molar percentages and two of them are presented in Table 5.

TABLE 5

| Composition of the different organic solutions prepared for formulations of TA-based (formulation E) or Partially PEGylated TA-based (formulation F) Tetra-Acidosomes | | | | |
|---|---|---|---|---|
| Formulation name | molar % of EggPC (mass %) | molar % of TA (mass %) | molar % of Partially PEGylated TA (mass %) | molar % of cholesterol (mass %) |
| E | 50<br>(62) | 5<br>(10) | 0<br>(0) | 45<br>(28) |
| F | 50<br>(47) | 0<br>(0) | 5<br>(32) | 45<br>(21) |

The organic phase was constituted of EtOH instead of MeOH as for formulations A-D in order to avoid potential toxicity problems induced by residual MeOH after the administration of formulations. Stock solutions of 4 $mg \cdot L^{-1}$ were prepared. Once the formulations were produced, the organic phase was removed by dialysis, and the liposomal solutions extracted from the dialysis. Tube (500 μL) were then analysed by DLS to get the Z-average in nm and the PDI (Table 6).

TABLE 6

| Z-average (nm) and PDI measured by DLS for the Tetra-Acidosomes formulations with natural TA lipids or partially PEGylated TA lipids at J and J + 21 days | | |
|---|---|---|
| Formulation name | E | F |
| Average size (nm) - J | 65.31 | 39.93 |
| Average size (nm) - J + 21 | n.d. | 44.21 |
| Average PDI - J | 0.172 | 0.162 |
| Average PDI - J + 21 | n.d. | 0.127 |

(n.d. = non-determined)

Firstly, liposomal solutions made from both TA lipids or partially PEGylated TA lipids associated with EggPC and/or cholesterol were obtained with hydrodynamic diameters lower than 100 nm. Moreover, the PDI for each formulation is good as it is always inferior to 0.2, which means that we were able to formulate monodisperse lipidic vesicles. Secondly, it was observed that the use of partially PEGylated TA lipids instead of natural TA lipids promoted the formation of even smaller vesicles, which should facilitate the liposome escape from the blood capillaries as well as the liposomal uptake into the targeted tissue [21]. More interestingly, partially PEGylated TA-based formulation was very stable. Indeed, after twenty-one days, the average diameter and PDI of the formulation remained almost unchanged.

LIST OF REFERENCES

1. Sonaje, K.; Chen, H. L.; Wey, S. P.; Juang, J. H.; Nguyen, H.-N.; Hsu, C. W.; Lin, K. J.; Sung, H. W., *Biomaterials* 2010, 31 (12), 3384-3394.
2. Benvegnu, T; Lemiègre, L.; Dalençon, S.; Jeftic, J., *Curr. Biotechnol.* 2013, 294-303.
3. G. Kaur, T. Garg, G. Rath, A M K. Goyal, *Drug Deliv.*, 2015, 23(7), 2497-2512.
4. Jensen, S. M.; Christensen, C. J.; Petersen, J. M.; Treusch, A. H.; Brandl, M., *Int. J. Pharm.* 2015, 493, (1-2), 63-69.
5. Li, Z.; Chen, J.; Sun, W.; Xu, Y., *Biochem. Biophys. Res. Commun.* 2010, 394, (2), 412-417.

6. Uhl, P.; Helm, F.; Hofhaus, G.; Brings, S.; Kaufman, C.; Leotta, K.; Urban, S.; Haberkorn, U.; Mier, W.; Fricker, G., *Eur. J. Pharm. Biopharm.* 2016, 103, 159-166.

7. Maisel, K.; Ensign, L.; Reddy, M.; Cone, R.; Hanes, J., *J. Control. Release* 2015, 197, 48-57.

8. Bode, M. I.; Buddoo, S. R.; Minnaar, S. H.; du Plessis, C. A., *Chem. Phys. Lipids* 2008, 154, (2), 94-104.

9. Benvegnu, T.; Lemiègre, L.; Cammas-Marion, S., *Eur. J. Org. Chem.* 2008, (28), 4725-4744.

10. T. D. Baugh, K. V. Grande, H. Mediaas, J. E. Vindstad and N. O. Wolf, *SPE International Symposium on Oilfield Scale*, SPE 93011 Aberdeen, United Kingdom, May 11-12, 2005.

11. Mediaas, H.; Grande, K.; Hustad, B.; Rasch, A.; Rueslatten, H.; Vinstad, J. E., 5$^{th}$ *International Symposium on Oilfiled Scale*, SPE 80404, Aberdeen, United Kingdom, Jan. 29-30, 2003.

12. Lutnaes, B. F.; Brandal, O.; Sjoblom, J., *Org. Biomol. Chem.* 2006, 4, (4), 616-620.

13. Lutnaes, B. F.; Krane, j.; Smith, B. E.; Rowland, S. J., *Org. Biomol. Chem.* 2007, 5, 1873-1877.

14. Benvegnu, T.; Réthoré, G.; Brard, M.; Richter, W., Plusquellec, D., Chem. Commun. 2005, 5536-5538

15. De, S.; Girigoswami, A., *J. Coll. Int. Sci.* 2004, 271, 485-495.

16. Zhang, X.; Chen, G.; Zhang, T.; Ma, Z.; Wu, B., *Int. J. Nanomed.* 2014, 9, 5503-5514.

17. Artursson, P.; Lundquist, P., *Nat. Biomed. Eng.*, 2020, 4, 12-13.

18. Simon, S.; Nordgård, E.; Bruheim, P.; Sjöblom, J., *J. Chromatogr. A* 2008, 1200, (2), 136-143

19. Barbeau, J., These: "Archaeaosomes et archaepolyosomes: synthése, formulation et vectorisation ciblée de peptides d'origine marine." *Univ. Rennes* 1 2009, 4060.

20. M. Berchel, J. P. Haelters, D. Afonso, A. Maroto, L. Deschamps, P. Giamarchi, P. A. Jaffrés, Eur. J. Org. Chem., 1076-1083, 2014.

21. M. Sharifi, W. C. Cho, A. Ansariesfahani, R. Tarharoudi, H. Malekisarvar, S. Sari, S. Haj Bloukh, Z. Edis, M. Amin, J. P. Gleghorn, T. L. M. ten Hagen, M. Falahati, Cancers, 2022, 14(12), 2868.

The invention claimed is:

1. Lipid compound having the following general formula (II):

(II)

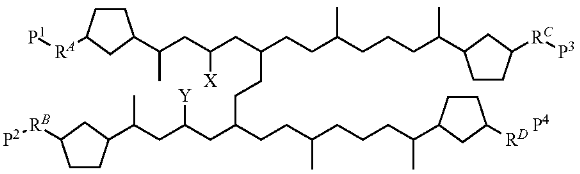

wherein $R^A$, $R^B$, $R^C$ and $R^D$ independently represent a linear or branched, aliphatic or alicyclic, saturated, hydrocarbon group comprising from 2 to 8 carbon atoms, $P^1$, $P^2$, $P^3$, and $P^4$ are the same or different, and each represents one of the following substituents:

$CH_2OH$;

COOH;

$COOR^1$, with $R^1$ which represents an aliphatic linear or branched, saturated or unsaturated alkyl chain with a number of carbon atoms between 1 to 22;

$A^1$-$CH_2$—$CH_2$—$N^+(CH_3)_3$, $X_2^-$, $X_2$ representing a halogen or a sulfonate, $A^1$ representing an ester (OC(O)) bond;

$A^2$-($PEG_{X1}$-$A^3$)-$R^2$, $PEGx_1$, being a polyethylene glycol of molecular weight X1, X1 being less than or equal to 5000 daltons, $A^2$ and $A^3$ being identical or different and representing an ester (C(O)O), an amide (C(O)NH), a triazole, $R^2$ representing a methoxy group, a targeting agent or a probe;

X and Y are independently H or $CH_3$;

wherein at least one of $P^1$, $P^2$, $P^3$, and $P^4$ is $A^1$-$CH_2$—$CH_2$—$N^+$—$(CH_3)_3$ or $A^2$-($PEG_{X1}$-$A^3$)-$R^2$ as defined above.

2. The lipid compound according to claim 1, wherein $P^1$, $P^2$, $P^3$, and $P^4$ are the same or different, and each represents one of the following substituents:

$A^1$-$CH_2$—$CH_2$—$N^+(CH_3)_3$, $X_2^-$, $X_2$ representing a halogen or a sulfonate, $A^1$ representing an ester (OC(O)) bond;

$A^2$-($PEG_{X1}$-$A^3$)$_n$-$R^2$, n being equal to 0 or 1, $PEGx_1$, being a polyethylene glycol of molecular weight X1, X1 being less than or equal to 5000 daltons, $A^2$ and $A^3$ being identical or different and representing an ester (C(O)O), an amide (C(O)NH), a triazole, $R^2$ representing a methoxy group, a targeting agent or a probe.

3. The lipid compound according to claim 1 having the following general formula (IIa), (IIb), (IIc), (IId), or (IIe):

(IIa)

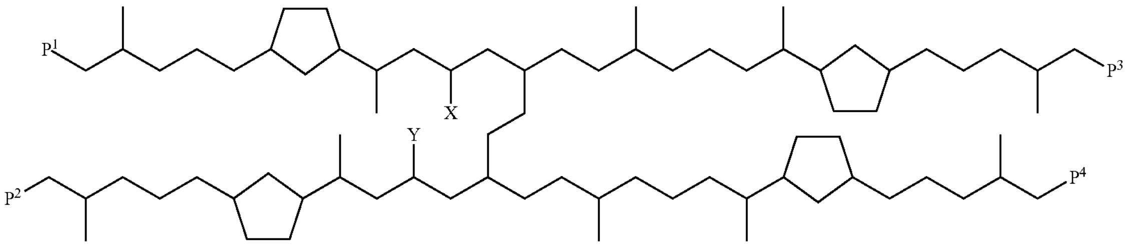

-continued (IIb)

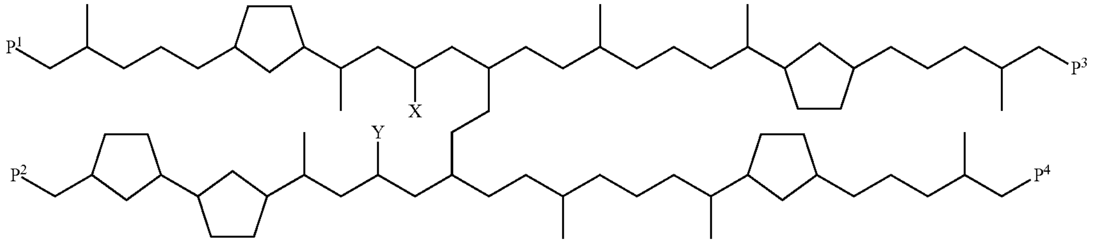

(IIc)

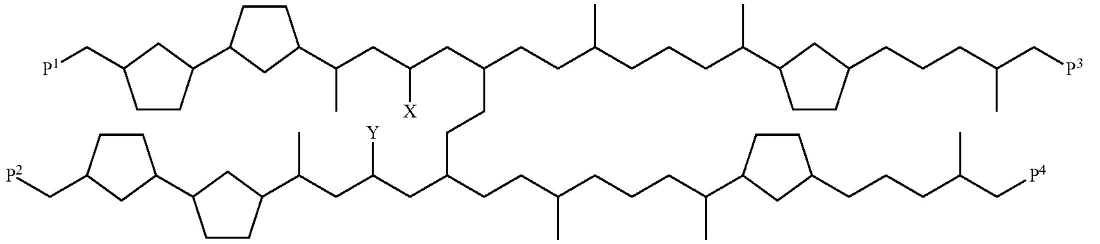

(IId)

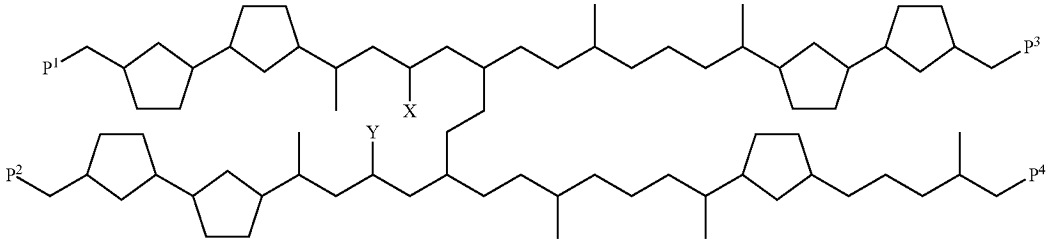

(IIe)

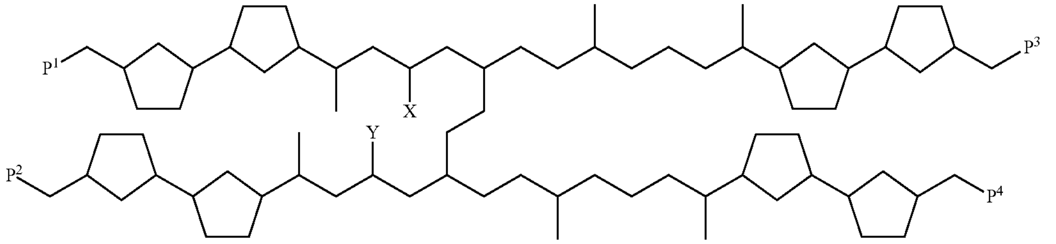

wherein

X, Y, $P^1$, $P^2$, $P^3$, and $P^4$ are as defined in claim 1.

4. Tetra-acidosome comprising a lipid compound having the following general formula (II):

(II)

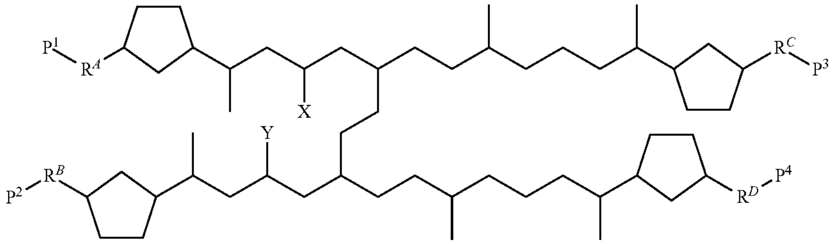

wherein $R^A$, $R^B$, $R^C$ and $R^D$ independently represent a linear or branched, aliphatic or alicyclic, saturated, hydrocarbon group comprising from 2 to 8 carbon atoms, $P^1$, $P^2$, $P^3$, and $P^4$ are the same or different, and each represents one of the following substituents:

$CH_2OH$;

COOH;

$COOR^1$, with $R^1$ which represents an aliphatic linear or branched, saturated or unsaturated alkyl chain with a number of carbon atoms between 1 to 22;

$A^1$-$CH_2$—$CH_2$—$N^+(CH_3)_3$, $X_2^-$, $X_2$ representing a halogen or a sulfonate, $A^1$ representing an ester (OC(O)) bond;

$A^2$-($PEG_{X1}$-$A^3$)-$R^2$, $PEGx_1$, being a polyethylene glycol of molecular weight X1, X1 being less than or equal to 5000 daltons, $A^2$ and $A^3$ being identical or different and representing an ester (C(O)O), an amide (C(O)NH), a triazole, $R^2$ representing a methoxy group, a targeting agent or a probe;

X and Y are independently H or $CH_3$; and at least one of $P^1$, $P^2$, $P^3$, and $P^4$ is $A^1$-$CH_2$—$CH_2$—$N^+(CH_3)_3$ or $A^2$-($PEG_{X1}$-$A^3$)-$R^2$ as defined above.

5. The tetra-acidosome according to claim 4, comprising a lipid compound having the following general formula (II) and wherein $P^1$, $P^2$, $P^3$, and $P^4$ are the same or different, and each represents one of the following substituents:

$A^1$-$CH_2$—$CH_2$—$N^+(CH_3)_3$, $X_2^-$, $X_2$ representing a halogen or a sulfonate, $A^1$ representing an ester (OC(O)) bond;

$A^2$-($PEG_{X1}$-$A^3$)$_n$-$R^2$, n being equal to 0 or 1, $PEGx_1$, being a polyethylene glycol of molecular weight X1, X1 being less than or equal to 5000 daltons, $A^2$ and $A^3$ being identical or different and representing an ester (C(O)O), an amide (C(O)NH), a triazole, $R^2$ representing a methoxy group, a targeting agent or a probe.

6. The tetra-acidosome according to claim 4, having an average size <250 nm.

7. The tetra-acidosome according to claim 4, having a polydispersity index (PDI)<0.3.

8. The tetra-acidosome according to claim 4, further comprising an encapsulated molecule of interest.

9. A method comprising: using the tetra-acidosome according to claim 4 as a carrier.

10. The method of claim 9, wherein using the tetra-acidosome comprises using the tetra-acidosome as a carrier to a gastrointestinal environment (GI).

11. A method comprising: administering the tetra-acidosome according to claim 4 to a subject in need thereof as a drug.

12. A method for the synthesis of a lipid compound as defined in claim 1 comprising a step of reacting a tetrameric acid (TA) lipid with a reducing agent, an alcohol, an amine or an ester.

13. The lipid compound according to claim 1, wherein $R^A$, $R^B$, $R^C$ and $R^D$ independently represent

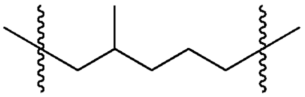
or
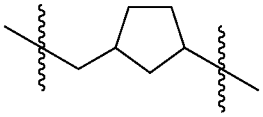
, in which  is the point of attachment to either $P^1$, $P^2$, $P^3$, and $P^4$ or the main molecule.

14. The lipid compound according to claim 1, wherein $R^1$ represents an aliphatic linear or branched, saturated or unsaturated alkyl chain with 4 carbon atoms.

15. The tetra-acidosome according to claim 4, wherein $R^A$, $R^B$, $R^C$ and $R^D$ independently represent

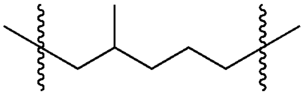
or
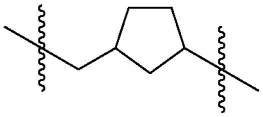
, in which  is the point of attachment to either $P^1$, $P^2$, $P^3$, and $P^4$ or the main molecule.

16. The tetra-acidosome according to claim 4, wherein $R^1$ which represents an aliphatic linear or branched, saturated or unsaturated alkyl chain with 4 carbon atoms.

* * * * *